United States Patent
Carranza et al.

(10) Patent No.: US 11,471,234 B2
(45) Date of Patent: Oct. 18, 2022

(54) DUAL AMNIOTIC AND PLACENTA FLUID MEASUREMENT PARTURITION DRAPE

(71) Applicant: Medline Industries, LP, Northfield, IL (US)

(72) Inventors: Angela Carranza, Racine, WI (US); Kate Pottala, Chicago, IL (US); Robert Taylor, Nashville, IN (US)

(73) Assignee: Medline Industries LP, Northfield, IL (US)

( * ) Notice: Subject to any disclaimer, the term of this patent is extended or adjusted under 35 U.S.C. 154(b) by 235 days.

(21) Appl. No.: 17/008,948

(22) Filed: Sep. 1, 2020

(65) Prior Publication Data
US 2022/0061945 A1    Mar. 3, 2022

(51) Int. Cl.
*A61B 46/20* (2016.01)
*A61B 90/00* (2016.01)
*A61B 17/42* (2006.01)

(52) U.S. Cl.
CPC .............. *A61B 46/20* (2016.02); *A61B 90/06* (2016.02); *A61B 17/42* (2013.01); *A61B 2046/201* (2016.02); *A61B 2090/063* (2016.02)

(58) Field of Classification Search
CPC ......... A61B 46/20; A61B 46/23; A61B 46/27; A61B 46/30; A61B 2046/201; A61B 2046/205; A61B 2046/234; A61B 2046/236; A61B 90/06; A61B 2090/063; A61B 17/42; B65D 31/12; B65D 31/142; B65D 33/24
USPC .................. 383/36, 38–40, 84–87, 93, 95
See application file for complete search history.

(56) References Cited

U.S. PATENT DOCUMENTS

| | | | |
|---|---|---|---|
| 4,076,017 A * | 2/1978 | Haswell | A61B 17/42 600/580 |
| 5,148,940 A * | 9/1992 | Mendise | A61B 50/36 229/101 |
| 5,339,831 A * | 8/1994 | Thompson | A61B 46/23 128/849 |
| 5,618,278 A | 4/1997 | Rothrum | |
| 5,916,202 A | 6/1999 | Haswell | |
| 6,199,553 B1 | 3/2001 | Hafer et al. | |
| 6,234,675 B1 * | 5/2001 | Saad | B65D 33/2541 383/102 |
| 7,556,429 B2 * | 7/2009 | Taheri | B65D 33/2566 383/38 |
| 7,690,380 B2 | 4/2010 | Lee et al. | |
| 2010/0137820 A1 | 6/2010 | Lee et al. | |
| 2011/0174318 A1 * | 7/2011 | Reyes | A61B 50/30 128/852 |

(Continued)

OTHER PUBLICATIONS

"Underbuttocks Drape w/ Pouch and Port", Published on or before May 12, 2020; Viewed online at https://www.medline.com/product/Underbuttocks-Drape-w/Pouch-and-...-Navigable-For-Boost/Z05-PF07229?question=&index=P1&indexCount=1.

(Continued)

*Primary Examiner* — Camtu T Nguyen
(74) *Attorney, Agent, or Firm* — Philip H. Burrus, IV

(57) ABSTRACT

A parturition drape (100) includes a drape (101) and a twin pouch assembly (102). The twin pouch assembly defines a first pouch (1101) and a second pouch (1301) attached to a major face of the drape. A flap (103) is attached to the major face of the drape. The flap (103) is selectively insertable into an open end of either the first pouch or the second pouch.

20 Claims, 9 Drawing Sheets

(56) References Cited

U.S. PATENT DOCUMENTS

2016/0015388 A1    1/2016  Ren
2016/0166323 A1*  6/2016  Tylka ..................... A61B 46/00
                                                                128/852

OTHER PUBLICATIONS

"Underbuttocks Surgical Drape with Pouch and Backing", Published on or before May 20, 2020; Viewed online https://www.medline.com/product/Underbuttocks-Surgical-Drape-with...Underbuttocks-Drapes/Z05-PF07228?question=&index=P2&indexCount=2.

* cited by examiner

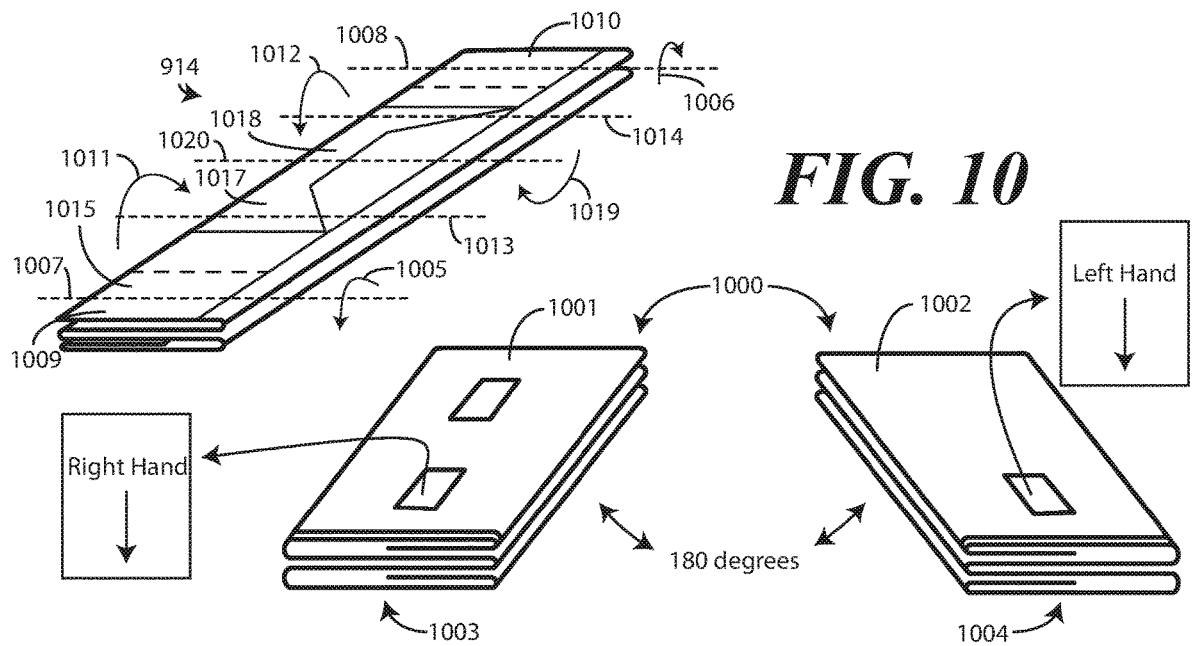
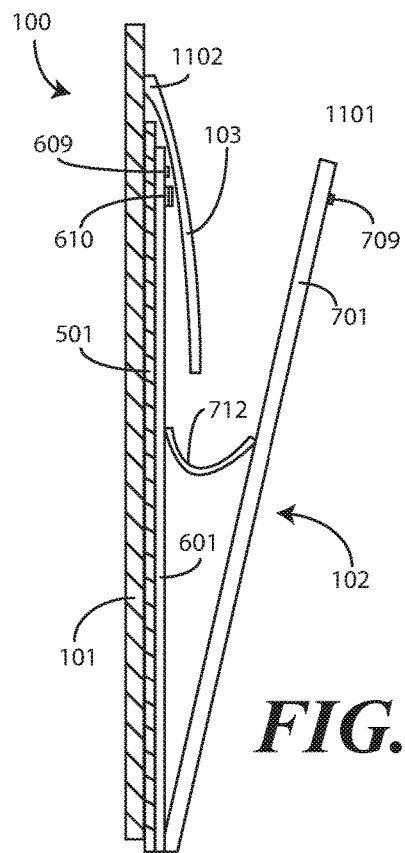
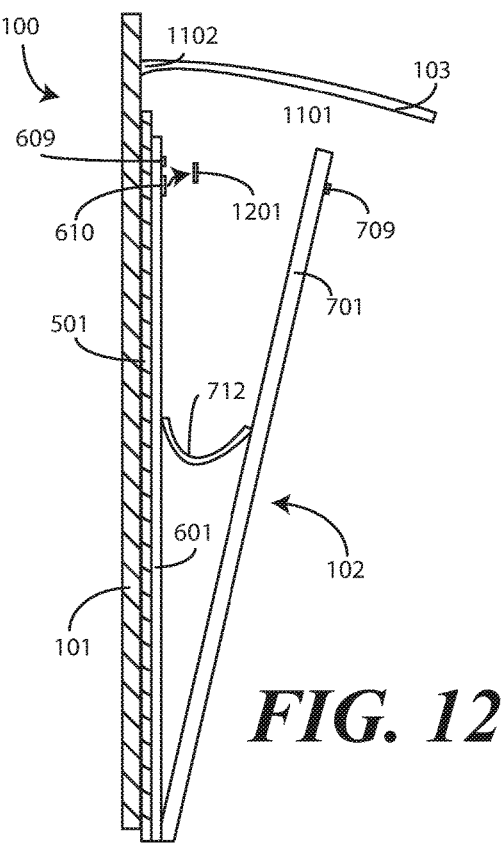

DUAL AMNIOTIC AND PLACENTA FLUID MEASUREMENT PARTURITION DRAPE

BACKGROUND

Technical Field

This disclosure relates generally to medical devices, and more particularly to medical drapes.

Background Art

Many medical procedures involve large amounts of fluid. Such fluids can be used in the procedure, e.g., irrigation fluids, or may emanate from the patient, e.g., blood left in the umbilical cord during childbirth. While absorptive or suction devices can be used to remove this fluid from the procedure site, collection is sometimes preferred. Illustrating by example, blood from the umbilical cord and placenta can include stem cells that can be collected and used in other medical procedures. It would be advantageous to have an improved medical device that simplified the collection of such fluids.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present disclosure.

FIG. 10 illustrates one or more additional explanatory method steps for folding an explanatory parturition drape in accordance with one or more embodiments of the disclosure.

FIG. 11 illustrates a sectional view of one explanatory parturition drape in a first state of use in accordance with one or more embodiments of the disclosure.

FIG. 12 illustrates a sectional view of one explanatory parturition drape in a second state of use in accordance with one or more embodiments of the disclosure.

Figure 1:
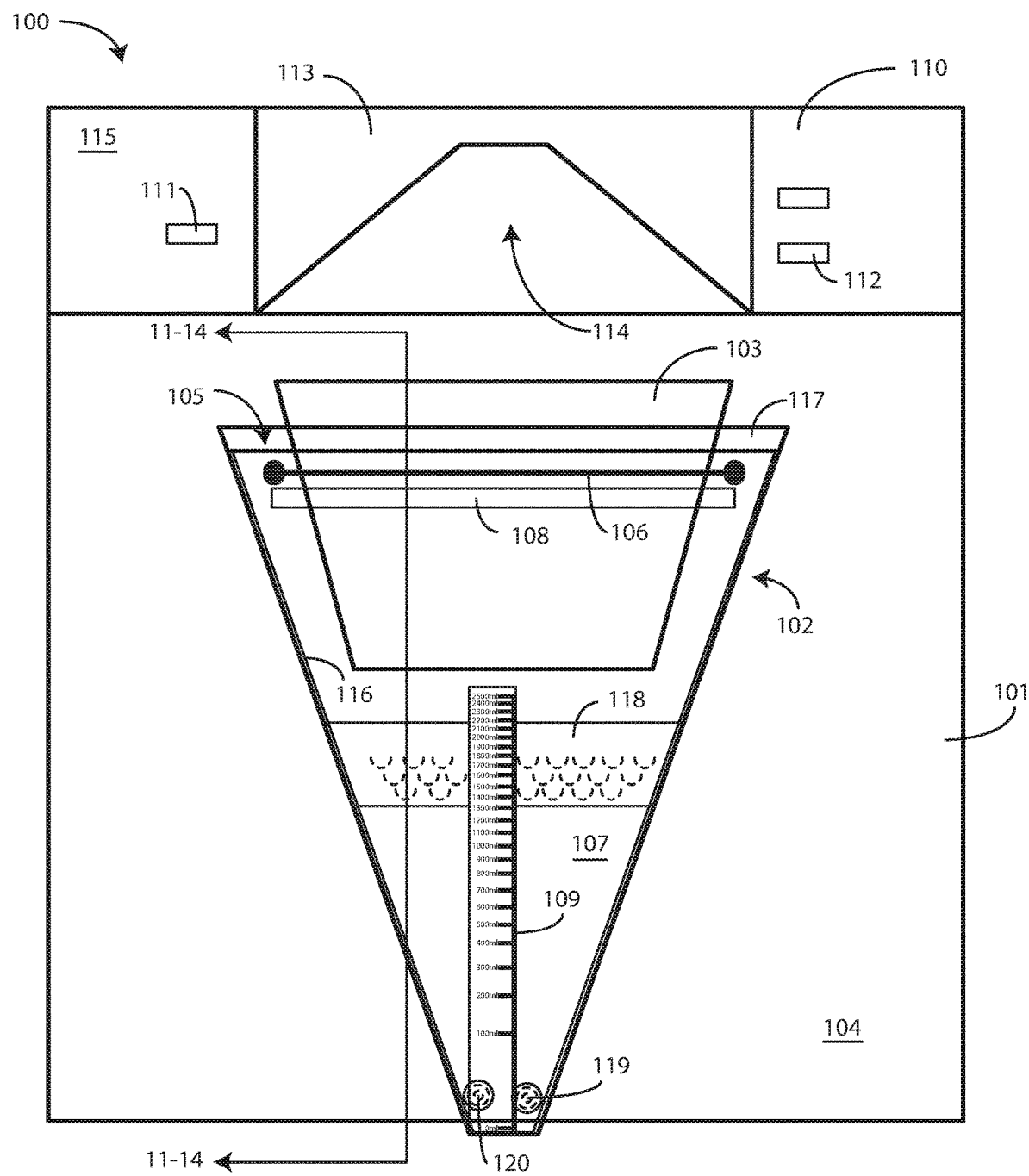
FIG. 1 illustrates one explanatory parturition drape in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Before describing in detail embodiments that are in accordance with the present disclosure, it should be observed that the embodiments reside primarily in combinations of method steps and apparatus components related to a parturition drape with a twin pouch assembly attached thereto. Alternate implementations are included, and it will be clear that method steps may be executed out of order from that shown or discussed, including substantially concurrently or in reverse order, depending on the functionality involved. Illustrating by example, FIGS. 2-8 illustrate the construction of one explanatory parturition drape that begins with a drape and continues with the attachment of each component in a stack so that the relevant components can most easily and visibly be illustrated in the drawings. However, in many embodiments the twin pouch assembly will be constructed as an independent unit and attached to the drape thereafter. This means that the method steps shown in FIGS. 6-8 may occur prior to those occurring in FIG. 3 or 5, for instance.

Accordingly, the apparatus components and method steps have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, it is expected that one of ordinary skill, notwithstanding possibly significant effort and many design choices motivated by, for example, available time, current technology, and economic considerations, when guided by the concepts and principles disclosed herein will be readily capable of performing such method steps for making and using parturition drapes in accordance with embodiments of the disclosure, in any order, with minimal experimentation.

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions.

As used herein, the terms "substantially", "essentially", "approximately", "about" or any other version thereof, are defined as being close to as understood by one of ordinary skill in the art, and in one non-limiting embodiment the term is defined to be within ten percent, in another embodiment within five percent, in another embodiment within 1 percent and in another embodiment within one-half percent. The term "coupled" as used herein is defined as connected, although not necessarily directly. The term "attached," by contrast, is used to refer to direct connections between components. Also, reference designators shown herein in parenthesis indicate components shown in a figure other than the one in discussion. For example, talking about a device (10) while discussing figure A would refer to an element, 10, shown in figure other than figure A.

An unfortunate statistic is that the United States leads the world in the number of post-partum maternal deaths. Some of these instances result from the fact that many births occur outside of the operating room. Such locations can mean that equipment to estimate blood lost by the mother is unavailable. Moreover, when nurses and other health care service providers are stretched for time while caring for a newborn infant, they may be unable to persistently monitor fluid lost by the mother during delivery.

Embodiments of this disclosure provide a solution to such problems. In one or more embodiments, a parturition drape comprises a drape. Attached to the drape is a twin pouch assembly. In one or more embodiments, the twin pouch assembly defines a first pouch and a second pouch. In one or more embodiments, the twin pouch assembly is attached to a major face of the drape.

To guide fluids emanating from a patient placed atop a portion of the drape into either the first pouch or the second pouch of the twin pouch assembly, in one or more embodiments the parturition drape includes a flap attached to the major face of the drape. In one or more embodiments, the flap is selectively insertable into an open end of either the first pouch or the second pouch.

In one or more embodiments, the twin pouch assembly includes a front panel, a rear panel, and an interior panel positioned between the front panel and the rear panel. In one or more embodiments, the front panel, interior panel, and rear panel are joined together by a perimeter seam that defines one or more closed sides of each of the first pouch and the second pouch, as well as an open end of each of the first pouch and the second pouch.

In one or more embodiments, a flexible strip can be attached to one or both of the front panel and/or the interior panel to retain the first pouch and the second pouch, respectively, in an open position when necessary. In one or more embodiments, an adhesive strip can be applied to the interior panel to couple an exterior surface of the interior panel to an interior surface of the front panel when the second pouch is in use.

In one or more embodiments, a graduated fluid measurement device can be positioned on the exterior of the front panel to allow for the measurement of amniotic fluid and/or placenta fluid as they are collected by the first pouch and second pouch. In one or more embodiments, the graduated fluid measurement device indicates a volume of fluid within the first pouch or the second pouch due to the fact that the front panel and interior panel are coextensive in area in one or more embodiments. Fluid drains can be positioned along the front panel or the rear panel to allow for fluids to be drained from the first pouch or second pouch, respectively.

Embodiments of the disclosure offer numerous advantages over prior art drapes. Illustrating by example, using prior art systems the estimation or calculation of blood lost by a mother during a vaginal birth occurs after both amniotic fluid and blood/placenta/tissue (referred to as "placenta fluid" herein) is collected in a single container. Using such a container prohibits a medical services provider from determining what the true volume of blood lost by the mother is. Embodiments of the disclosure contemplate that after the amniotic sac is punctured or ruptured, fluid flowing from the mother is predominantly amniotic fluid. Thereafter, the predominant component of fluid and/or solids flowing from the mother is from the placenta, umbilical cord, and the mother herself.

Accordingly, in one or more embodiments the amniotic fluid is first captured in a first pouch of the twin pouch assembly. Thereafter, blood and/or tissue, "placenta fluid," can be collected in the second pouch of the twin pouch assembly. Advantageously, embodiments of the disclosure allow for a single parturition drape to provide a twin pouch assembly that offers a simple transition from collecting amniotic fluid to capturing placenta fluid for blood loss measurements. In use, the twin pouch assembly allows the first pouch and second pouch to store each type of fluid separately, thereby allowing the health care services provider to visually assess quickly if emergent maternal care needs to be activated.

In one or more embodiments, parturition drapes constructed in accordance with embodiments of the disclosure provide for accurate measurement of fluids emanating from a mother during vaginal child delivery. The twin pouch assembly, which includes the first pouch and the second pouch, has two separate features. A first supports collection and measurement of the volume of amniotic fluid discharged prior to the delivery of the baby. A second then supports collection and an accurate measurement of the volume of blood emanating from the delivery of placenta. Advantageously, embodiments of the disclosure make it easier for health care service providers to visually see the separated fluid sacs, as well as make medical assessments using the graduated fluid measurement device positioned on the exterior of the twin pouch assembly. This allows the health care services provider to better determine whether the blood loss recorded during delivery requires further medical attention to the mother. Other advantages will be described below. Still others will be obvious to those of ordinary skill in the art having the benefit of this disclosure.

Turning now to FIG. 1, illustrated therein is one explanatory parturition drape 100 in accordance with one or more embodiments of the disclosure. In one or more embodiments, the parturition drape 100 includes a drape 101. A twin pouch assembly 102 defining a first pouch and a second pouch are attached to a major surface 104 of the drape 101.

In one or more embodiments, a flap 103 is also attached to the major surface 104 of the drape 101. In one or more embodiments, the flap 103 is selectively insertable into an open end 105 of either the first pouch or the second pouch of the twin pouch assembly 102 so as to guide fluids passing down the major surface 104 of the drape 101 into the first pouch or second pouch as desired.

In one or more embodiments, a flexible strip 106 is attached to an exterior 107 of the front panel of the twin pouch assembly 102. In one or more embodiments, the flexible strip 106 is configured to retain the first pouch of the twin pouch assembly 102 in an open position while the flap 103 is inserted into the first pouch of the twin pouch assembly 102. As will be described below with reference to FIG. 6, in one or more embodiments another flexible strip is attached to an exterior of the interior panel of the twin pouch assembly 102. The other flexible strip is configured to retain the second pouch of the twin pouch assembly 102 in an open position while the flap 103 is inserted into the second pouch of the twin pouch assembly 102.

In one or more embodiments, an adhesive strip 108 can also be attached to an exterior surface of the interior panel of the twin pouch assembly 102. After the first pouch of the twin pouch assembly 102 is used, for example, the adhesive strip 108 can be used to retain the exterior surface of the interior panel of the twin pouch assembly 102 against an interior surface of the front panel of the twin pouch assembly 102 via adhesive coupling. This will be described in more detail below with reference to FIGS. 12-14.

In one or more embodiments, a graduated fluid measurement device 109 is positioned at the exterior of the twin pouch assembly 102. In one or more embodiments, the graduated fluid measurement device 109 indicates a volume of fluid situated in the first pouch of the twin pouch assembly 102 or the second pouch of the twin pouch assembly 102. Advantageously, this graduated fluid measurement device 109, when used in conjunction with the twin pouch assembly 102, allows a health care services provider to accurately measure both amniotic fluid guided into one of the first pouch or the second pouch of the twin pouch assembly 102 by the flap 103 and blood and/or placenta fluids guided into another of the first pouch or the second pouch of the twin pouch assembly 102 by the flap 103.

In the illustrative embodiment of FIG. 1, an upper edge of the drape 101 is folded such that a first portion of the first major surface 104 of the drape 101 abuts another portion of the first major surface 104 of the drape 101. Ultrasonic bonding, thermal bonding, adhesive bonding, or other bonding can then be applied to retain this portion of the drape 101 folded. This results in the upper edge of the drape 101 defining a cuff 110 positioned along an edge of the drape 101. The formation of the cuff 110 will be described in more detail with reference to FIG. 3 below. In one or more embodiments, a health care services provider can place their hands inside the cuff 110 to unfold the parturition drape 100 without compromising the sterile field occurring along the first major surface 104 of the drape 101. Labels 111,112 can be applied to exterior surfaces of the cuff 110 to indicate this, as will be described in more detail below with reference to FIG. 10.

In one or more embodiments, a panel of reinforcing material 113 can be applied to the exterior surface of the cuff 110. Illustrating by example, a non-woven fabric can be used as the reinforcing material 113. Examples of non-woven fabrics suitable for use as the reinforcing material 113 include spunlace, spunbond, and blends of polyester, polypropylene, and/or polyethelene, as well as combinations thereof. Other materials suitable for use will be obvious to those of ordinary skill in the art having the benefit of this disclosure. Since the cuff 110 is formed by folding the drape 101 at its upper edge in this illustrative embodiment, the panel of reinforcing material 113 is attached to the rear major surface 115 of the drape 101 in FIG. 1

When the parturition drape 100 is in use, a patient can be positioned atop the cuff 110, with the cuff 110 serving as an underbuttocks portion of the parturition drape 100. The patient's buttocks can be placed atop the panel of reinforcing material 113 in one or more embodiments.

Since the parturition drape 100 is designed for use during childbirth, in one or more embodiments the panel of reinforcing material 113 defines a frustoconical recess 114 at the bottom edge of the panel of reinforcing material 113. As used herein, the term "frustoconical" takes its ordinary, plain, English definition of "having the shape of a frustum of a cone." A "frustum" of a cone, of course, is the portion of a cone or pyramid that lies between two parallel planes cutting it. The frustoconical recess 114 is therefore frustoconical because it includes two parallel sides (a second side defined by the opening of the recess) and two inwardly tapering sides like a frustum. In the illustrative embodiment of FIG. 1, the frustoconical recess 114 faces the twin pouch assembly 102.

When the parturition drape 100 is in use, a patient can be placed atop the cuff 110. The portions of the drape 101 extending from the cuff 110 can then be allowed to hang from a table, bed, or other horizontal surface such that fluids contacting the cuff 110 in the frustoconical recess 114 are directed along the flap 103 and into the appropriate pouch of the twin pouch assembly 102. Using the flexible strip 106, the desired pouch of the twin pouch assembly 102 can be opened and maintained in the open position. Accordingly, discharged fluids will be directed from the cuff 110, along the first major surface 104 of the drape 101, along the flap 103, and into the appropriate pouch of the twin pouch assembly 102, where they may be stored or removed using the first drain 119 or second drain 120.

In the illustrative embodiment of FIG. 1, the twin pouch assembly 102 has an inverted frustoconical shape. In one or more embodiments, the wider, upper end of the inverted frustoconical shape defines the open end 105 of the twin pouch assembly 102, while the narrower, lower end and inwardly tapering side surfaces are closed by a perimeter seam 116. As will be explained in more detail below with reference to FIGS. 2-7, in one or more embodiments the twin pouch assembly 102 is constructed from a front panel, an interior panel, and a rear panel. In one or more embodiments, the front panel and the interior panel are coextensive, while the front panel has a length that is greater than that of the front panel and the interior panel.

Where the front panel, interior panel, and rear panel are joined together with the perimeter seam 116, this results in the rear panel being positioned between the drape 101 and the interior panel, and the interior panel being positioned between the front panel and the rear panel. Since the panels are configured to be coextensive in one or more embodiments, with the exception of the extra length 117 of the rear panel, this results in the twin pouch assembly 102 defining a second pouch that is situated between the drape 101 and a first pouch. The extra length 117 of the rear panel can be used as an attachment strip to adhesively, thermally, ultrasonically, or otherwise attach the twin pouch assembly 102 to the first major surface 104 of the drape 101 in one or more embodiments.

In one or more embodiments, each of the first pouch of the twin pouch assembly 102 and the second pouch of the twin pouch assembly 102 can be fitted with a drain so that fluids can be drained from the first pouch or the second pouch. Illustrating by example, in FIG. 1 the twin pouch assembly includes a first drain 119 to allow for fluid to be drained from the first pouch of the twin pouch assembly 102 and a second drain 120 to allow fluids to drain from the second pouch of the twin pouch assembly 102. In this illustrative embodiment, since the second pouch is situated between the drape 101 and the first pouch, the first drain 119 is exposed on a side of the twin pouch assembly 102 opposite the drape 101, i.e., out of the page as viewed in FIG. 1, while the second drain 120 is exposed on the side of the twin pouch assembly 102 facing the drape 101, i.e., into the page as viewed in FIG. 1.

In one or more embodiments, one or both of the first pouch of the twin pouch assembly 102 or the second pouch of the twin pouch assembly 102 can be configured with a sieve 118 to catch and collect any tissue, non-liquids, instruments, sponges, or other medical implements so they can be retrieved prior to measuring any fluid using the graduated fluid measurement device 109. In one or more embodiments, a first sieve is positioned within the first pouch and a second sieve is positioned within the second pouch, as will be explained in more detail below with reference to FIGS. 6-7.

In one or more embodiments, each sieve includes a plurality of perforations, which can be configured as one or more of slits or small holes that to allow the passage of fluids into the lower portions of the twin pouch assembly 102 while retaining solid objects within the upper portion of the twin pouch assembly 102. In the illustrative embodiment of FIG. 1, the sieve 118 comprises a plurality of semi-circular perforations that allow fluids to pass through the sieve 118 while catching solid objects. Where two sieves are included, a first sieve is coupled between the front panel and the interior panel of the twin pouch assembly 102, while a second sieve is coupled between the interior panel and rear panel of the twin pouch assembly 102. In one or more embodiments, each sieve is expandable so that it can expand when the first pouch or second pouch is opened, but collapse when the first pouch or second pouch is closed, and so forth. One illustrative sieve 118 suitable for use with the parturition drape 100 will be described below with reference to FIG. 17.

Figure 3:
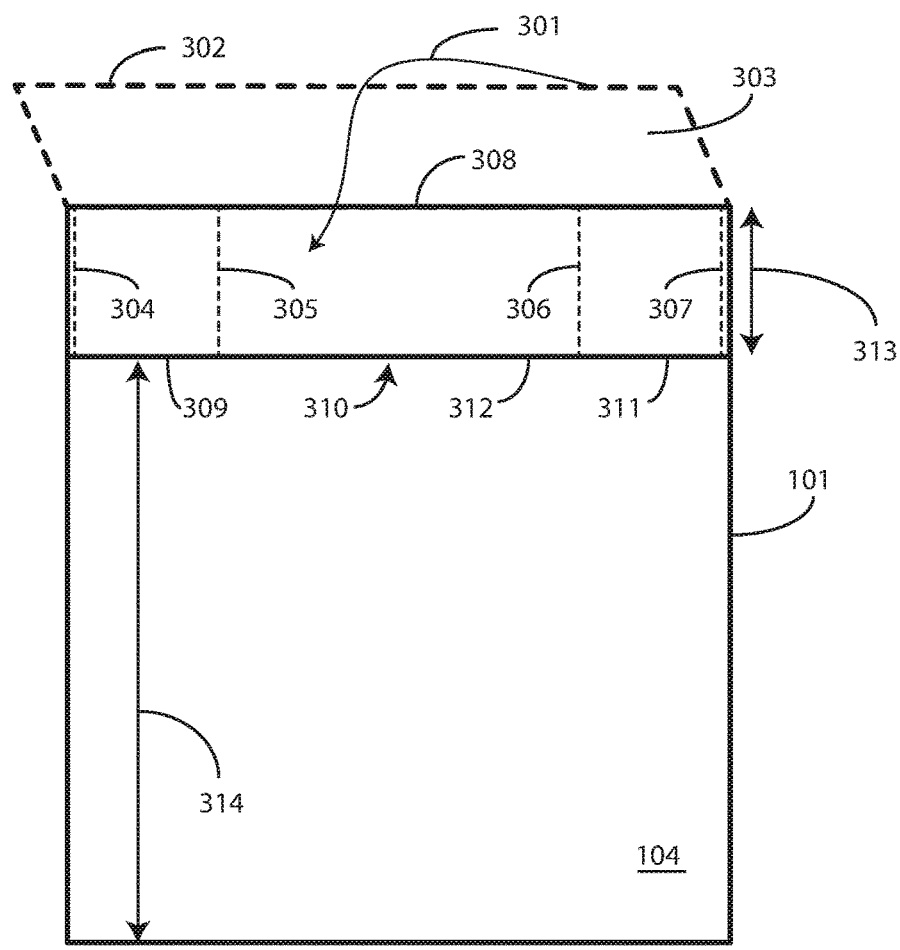
FIG. 3 illustrates one explanatory partially constructed parturition drape in accordance with one or more embodiments of the disclosure.
Figure 4:
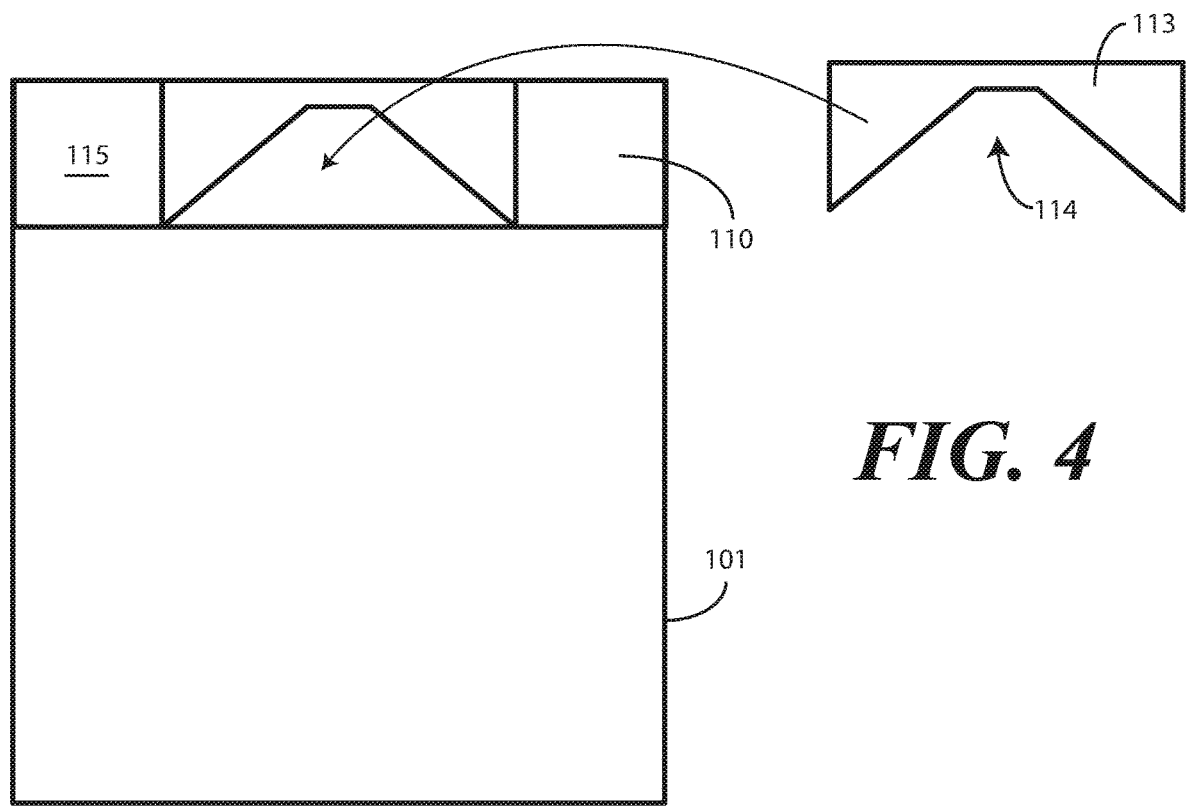
FIG. 4 illustrates another explanatory partially constructed parturition drape in accordance with one or more embodiments of the disclosure.
Figure 5:
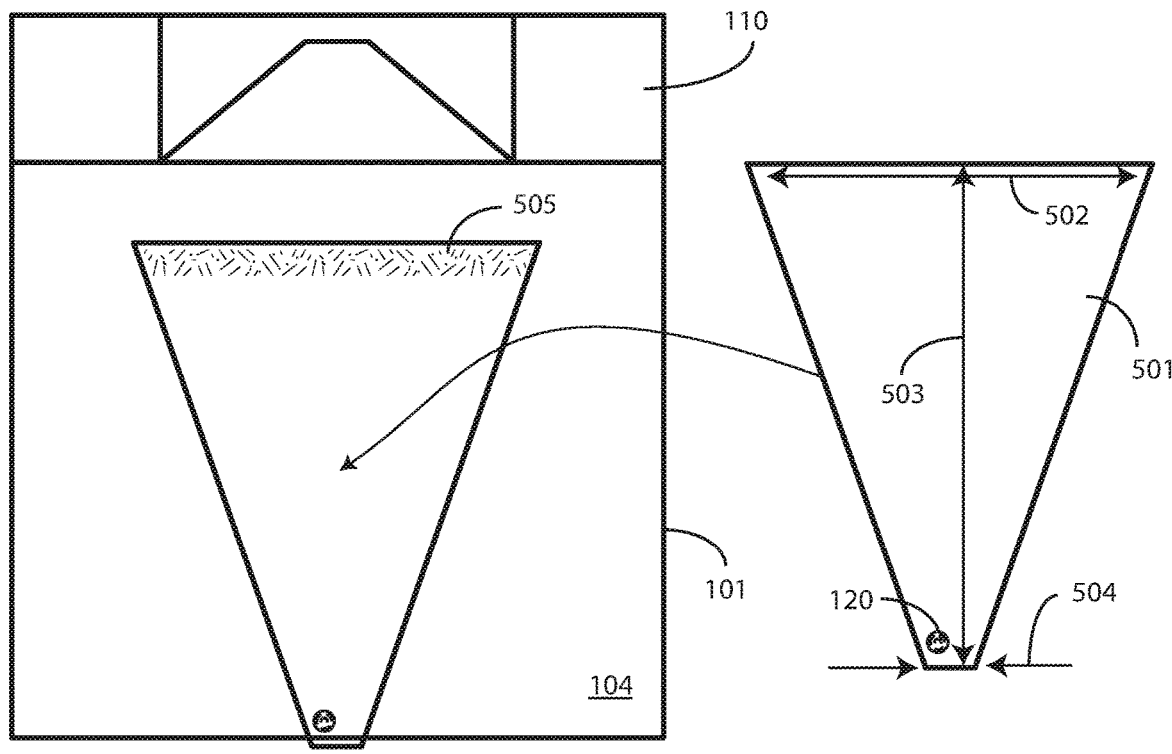
FIG. 5 illustrates another explanatory partially constructed parturition drape in accordance with one or more embodiments of the disclosure.

Turning now to FIGS. 2-8, one or more steps of constructing a parturition drape in accordance with embodiments of the disclosure will be described. The steps in FIGS. 2-8 are ordered for optimal visibility of each component. Illustrating by example, FIG. 5 shows the attachment of a rear panel to the drape prior to the interior panel or front panel being coupled to the rear panel. However, as noted above, the parturition drape can, and frequently will be, constructed using the steps of FIGS. 2-8 but in a different order than that used for illustration. For instance, in many situations the twin pouch assembly will be constructed as an independent unit and attached to the drape thereafter. This means that the method steps shown in FIGS. 6-8 may occur prior to those occurring in FIG. 3 or 5, for instance. Accordingly, the order of the steps of FIGS. 2-8 is but one order that will be obvious to those of ordinary skill in the art having the benefit of this disclosure.

Figure 2:
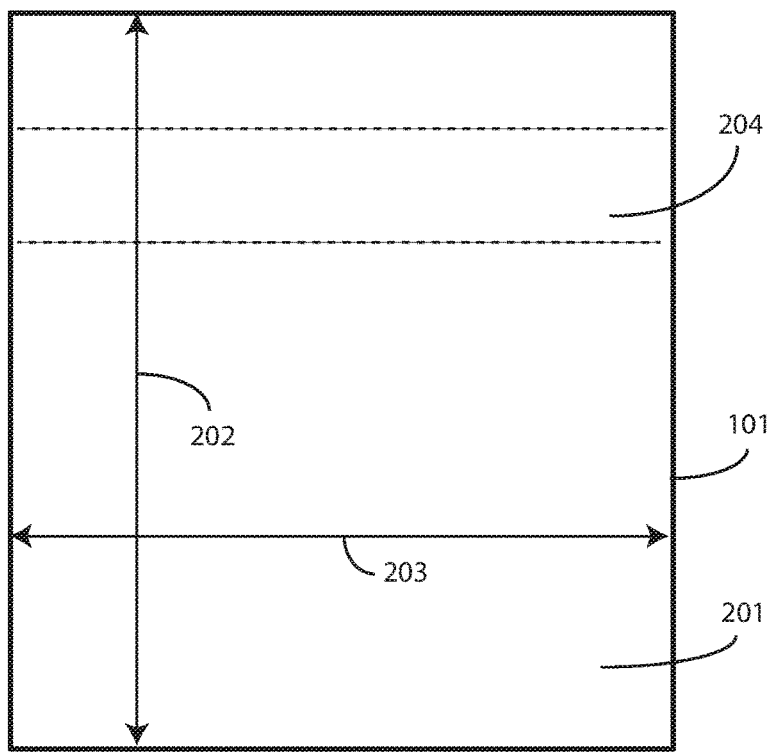
FIG. 2 illustrates one explanatory drape in accordance with one or more embodiments of the disclosure.

Beginning at FIG. 2, a drape 101 is provided. In one or more embodiments, the drape 101 comprises a layer 201 of material that is generally water resistant or waterproof. In one or more embodiments, the layer 201 of material comprises a single layer of material. For instance, the layer 201 of material can be a single layer of polyethylene or polyurethane. Illustrating by example, in one or more embodiments the layer 201 of material is manufactured from 0.065 millimeter, blue polyethylene. In other embodiments, the layer 201 of material can be a multi-ply layer of material.

In one or more embodiments, the layer 201 of material is manufactured from a disposable material. Examples of disposable material suitable for manufacturing the layer 201 include polyethylene, polyurethane, and other thermoplastic materials. Illustrating by example, in one or more embodiments the layer 201 of material is manufactured from polyethylene. In another embodiment, the layer 201 of material is manufactured from polypropylene. In yet another embodiment, the layer 201 of material is manufactured from a non-woven fabric that is coated with polyethylene, polypropylene, or another fluid resistant coating. In still another embodiment, the layer 201 of material is manufactured from Tyvek.sup™. One or more antimicrobial layers can be added to the layer 201 of material to further enhance antimicrobial protection.

Numerous other fabrics suitable for the layer 201 of material will be obvious to those of ordinary skill in the art having the benefit of this disclosure. For example, in another embodiment the layer 201 of material can be manufactured from a non-woven fabric. The non-woven fabric can be disposable in one or more embodiments. The non-woven fabric can optionally include a water resistant lining that prevents the passage of fluids through the layer 201 of material in one or more embodiments.

Illustrating by example, in one or more embodiments the layer 201 of material is manufactured from a water-repellent or water-impermeable material and/or is coated with such a water-repellent or water impermeable material to prevent the passage of fluids. For example, the layer 201 of material can include various woven, non-woven, hydroentangled materials, and/or combinations thereof. The layer 201 of material may include absorbent Airlaid, spunlace, blends of polyester, polypropylene, polyethylene, urethane, and/or combinations thereof. The layer 201 of material may be manufactured using various methods, including a spunbond meltblown spunbond (SMS) method, a spunbond meltblown meltblown spunbond method (SMMS), and a spunbond meltblown meltblown spunbond method (SMMMS). The layer 201 of material can further be coated with fluid resistant linings, such as polyethylene or polypropylene.

In one embodiment, the drape 101 is opaque. The drape 101 can be color-coded to indicate that it is designed for a particular procedure as well. For example, a particular color such as blue may indicate that the drape 101 is to be used for parturition procedures. Other color codings will be obvious to those of ordinary skill in the art having the benefit of this disclosure.

In one or more embodiments, the 101 has a length 202 of between 45 and 60 inches, such as about 53.5 inches plus or minus an inch. In one embodiment, the drape 101 has a width 203 of about forty inches, plus or minus one inch. The term "about" is used to refer to a measurement inclusive of manufacturing tolerances. Accordingly, both 52.7 and 54.1 inches would be "about" 53.5 inches if the manufacturing tolerances were plus or minus one inch.

In one embodiment, pockets or other surface features, none of which is shown in FIG. 2 for simplicity, but that will be obvious to those of ordinary skill in the art having the benefit of this disclosure, can be attached to the layer 201 of material. As noted above, the layer 201 of material may be manufactured in various colors. In one or more embodiments where the drape 101 manufactured from the layer 201 of material is used in medical applications, the layer 201 of material can be blue or yellow. Yellow is a color particularly well suited for medical procedures due to its high visibility and easy differentiation from a person's skin. Blue is advantageous because it can immediately identify the gown as a medical gown manufactured by a particular manufacturer and/or a particular type of procedure, as noted above.

Turning now to FIG. 3, illustrated therein is the drape 101 being folded 301 to create a cuff 110. As noted above, in one or more embodiments an upper edge 302 of the drape 101 is folded 301 such that a first portion 303 of the first major surface 104 of the drape 101 abuts another portion (204) of the first major surface 104 of the drape 101. Ultrasonic bonding, thermal bonding, adhesive bonding, or other bonding can then be applied along one or more seams 304, 305, 306, 307 to retain this portion 303 of the drape 101 in the folded configuration.

In one or more embodiments, this results in the upper portion of the drape 101 defining the cuff 110 positioned along an upper edge 308 of the drape 101. In one or more embodiments, the cuff 110 defines a continuous, closed end along the upper edge 308 of the drape 101, and one or more openings 309, 310, 311 along the lower edge 312 of the cuff 110. In one or more embodiments, at lest two openings 309,311 are included along the lower edge 312 of the cuff 110 to allow a health care services provider to insert their hands beneath the cuff 110 to unfold the drape 101 without compromising the sterile field. In the illustrative embodiment of FIG. 1, the lower edge 312 of the cuff 110 includes three openings 309, 310, 311. However, in other embodiments opening 310 will be sealed with a seam.

In one or more embodiments, when the cuff 110 is created, the cuff 110 has a length 313 of between eight and ten inches. In one or more embodiments, the length 313 of the cuff 110 is about nine inches. In one or more embodiments, the portion of the drape 101 extending distally from the cuff 110 has a length 314 of between forty-three and forty-six inches. Illustrating by example, in one or more embodiments the length 314 of the portion of the drape 101 extending distally from the cuff 110 is about 44.5 inches, plus or minus one inch. Other lengths will be obvious to those of ordinary skill in the art having the benefit of this disclosure.

Turning now to FIG. 4, in one or more embodiments a panel of reinforcing material 113 can be applied to the exterior surface of the cuff 110, which is the rear major surface 115 due to the folding (301) operation performed in FIG. 3 in this illustrative embodiment. In one or more embodiments, the reinforcing material 113 is attached to a rear major surface 115 of the drape 101 atop the cuff 110.

Illustrating by example, in one or more embodiments a panel of non-woven fabric is applied to the exterior surface of the cuff 110 using thermal bonding, ultrasonic bonding, adhesive bonding, or other bonding technologies. While shown being applied to the exterior surface of the cuff 110 after the cuff 110 is created in FIG. 4, in other embodiments the panel of reinforcing material 113 will be applied to the rear major surface 115 of the drape 101 prior to the folding (301) operation of FIG. 3. In still other embodiments, the cuff 110 can be formed by as separate layer of material that is bonded to the drape 101. Where this is the case, the panel of reinforcing material 113 can be attached to this layer prior to the cuff 110 being created.

In one or more embodiments, the panel of reinforcing material 113 comprises a non-woven fabric that increases friction along the exterior of the cuff 110 so that a patient sitting on the panel of reinforcing material 113 is less prone to slide along the cuff 110. Examples of non-woven fabrics suitable for use as the reinforcing material 113 include spunlace, spunbond, and blends of polyester, polypropylene, and/or polyethelene, as well as combinations thereof. Other materials suitable for use will be obvious to those of ordinary skill in the art having the benefit of this disclosure. When the parturition drape 100 is in use, a patient can be positioned atop the cuff 110, with the cuff 110 serving as an underbuttocks portion of the parturition drape 100. The patient's buttocks can be placed atop the panel of reinforcing material 113 in one or more embodiments.

Since the parturition drape 100 is designed for use during childbirth, in one or more embodiments the panel of reinforcing material 113 defines a frustoconical recess 114 at the bottom edge of the panel of reinforcing material 113. Fluids contacting the cuff 110 within the frustoconical recess 114 are configured to slide along the drape 101 toward the twin pouch assembly (102) as described below.

Turning now to FIG. 5, illustrated therein is a rear panel 501 of a twin pouch assembly (102) being attached to the first major surface 104 of the drape 101. In this illustrative embodiment, the rear panel 501 has an inverse frustoconical shape. The frustoconical shape is "inverse" because its narrow end projects downward and away from the portion of the drape 101 upon which a person will sit, which is the cuff 110 in this illustrative example.

In one or more embodiments, the wide end of the inverse frustoconical shape has a width 502 of between twenty-eight and thirty inches. For example, in one or more embodiments the wide end of the inverse frustoconical shape has a width 502 of about twenty-nine inches.

In one or more embodiments the length 503 of the inverse frustoconical shape is between thirty and thirty-four inches. For example, in one or more embodiments the length 503 of the inverse frustoconical shape is about thirty-two inches.

In one or more embodiments, the narrow end of the inverse frustoconical shape has a width 504 of between two and four inches. For example, in one or more embodiments the narrow end of the inverse frustoconical shape has a width 504 of about three inches. These measurements are illustrative only, as others will be obvious to those of ordinary skill in the art having the benefit of this disclosure.

In one or more embodiments, a drain 120 is coupled to the rear panel 501 of the twin pouch assembly (102) to allow fluids to be drained from the second pouch that will be partially defined by the rear panel 501. In this illustrative embodiment, since the rear panel 501 has the inverse frustoconical shape, with its narrowing end, the drain 120 is offset to the left of center along the rear panel 501 and is disposed at the bottom of the inverse frustoconical shape. This offset allows a front panel, described below with reference to FIG. 7, to have a drain that is offset to the other side of center.

The rear panel 501 can be attached to the first major surface 104 of the drape 101 in a variety of ways. In one or more embodiments, the rear panel 501 is attached to the drape 101 by thermal bonding. In another embodiment, the rear panel 501 is attached to the drape 101 by ultrasonic welding. In the illustrative embodiment of FIG. 5, the rear panel 501 is attached to the first major surface 104 of the drape 101 by an adhesive coupling 505. Other techniques for coupling the rear panel 501 to the first major surface 104 of the drape 101 will be obvious to those of ordinary skill in the art having the benefit of this disclosure.

In one or more embodiments, the rear panel 501 is optically transparent so that fluids positioned within the second pouch defined by the rear panel 501 can be seen. Said differently, in one or more embodiments the rear panel 501 is pellucid, and forms a transparent portion of the twin pouch assembly (102). Illustrating by example, in one or more embodiments the rear panel 501 can be manufactured from 0.06-millimeter clear polyethylene so as to be translucent or pellucid. In one or more embodiments, the rear panel 501 is manufactured from clear 0.06 mm polyethylene sheeting. It should be noted that other clear, flexible materials may be used in place of polyethylene.

In one or more embodiments, the adhesive coupling 505 is attached to the wide end of the inverted frustoconical shape of the rear panel 501 between the drape 101 and the rear surface of the rear panel 501. In one embodiment, the adhesive coupling 505 is a layer of adhesive tape with a width of about one inch.

Figure 6:
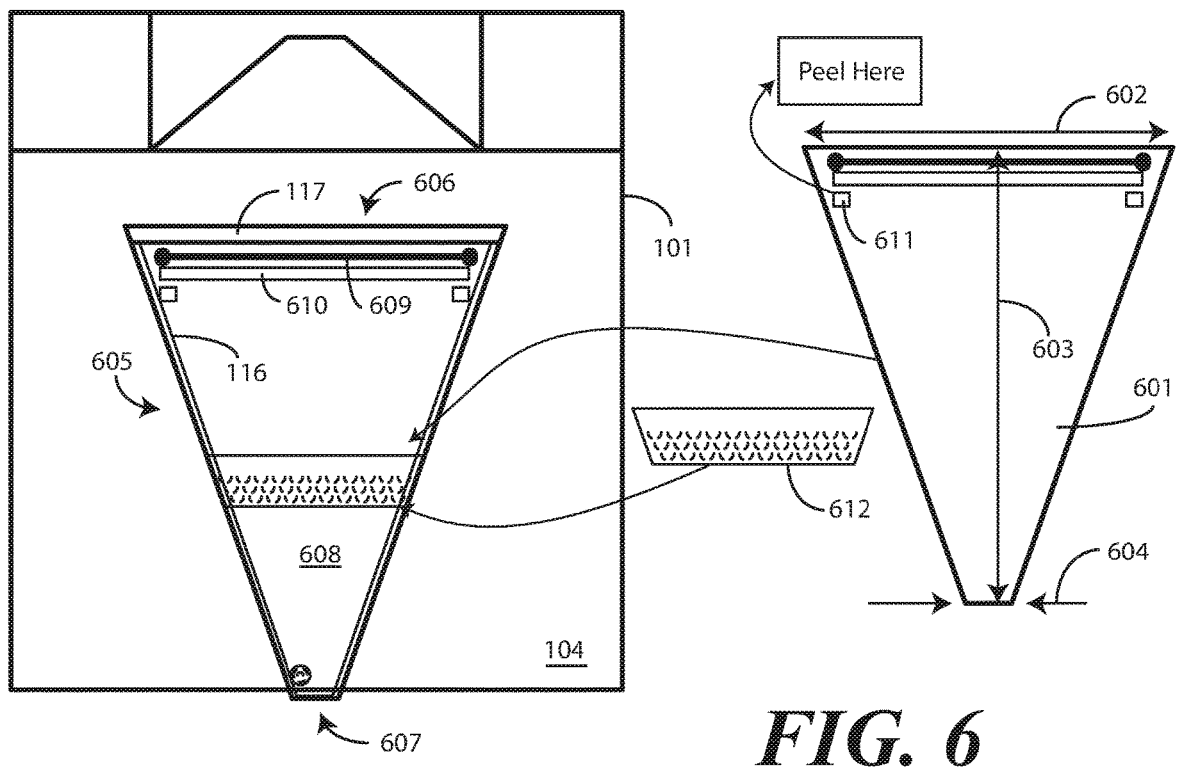
FIG. 6 illustrates another explanatory partially constructed parturition drape in accordance with one or more embodiments of the disclosure.

Turning now to FIG. 6, illustrated therein is an interior panel 601 of a twin pouch assembly (102) being attached to the rear panel (501) on a side of the rear panel (501) opposite the drape 101. This results in the rear panel (501) being positioned between the drape 101 and the interior panel 601.

In this illustrative embodiment, the interior panel 601 also has an inverse frustoconical shape. While the rear panel (501) and interior panel 601 of the illustrative embodiments of FIGS. 5-6 are inverse frustoconical in shape, it should be noted that they could take other shapes as well. For example, each of the rear panel (501) and interior panel 601 could be U-shaped, rectangularly shaped, triangularly shaped, or take other shapes. Additionally, while shown as having a common shape, namely, the inverse frustoconical shape of FIGS. 5-6, in other embodiments the rear panel (501) and the interior panel 601 could have different shapes.

In one or more embodiments, the interior panel 601 has a length 603 that is less than that of the rear panel (501). This results in the wide end of the inverse frustoconical shape having a width 602 that is less than the width (502) of the wide end of the rear panel (501). The extra length 117 of the rear panel (501) can be used for the adhesive coupling (505) to adhesively attach the twin pouch assembly (102) that will be constructed using the rear panel (501) and the interior panel 601 to the first major surface 104 of the drape 101 in one or more embodiments.

In one or more embodiments, the wide end of the inverse frustoconical shape has a width 602 of between twenty-seven and twenty-nine inches. For example, in one or more embodiments the wide end of the inverse frustoconical shape has a width 602 of about twenty-eight inches. In one or more embodiments the length 603 of the inverse frustoconical shape is between thirty and thirty-two inches. For example, in one or more embodiments the length 603 of the inverse frustoconical shape is about thirty inches.

In one or more embodiments, the narrow end of the inverse frustoconical shape has a width 604 that is the same as the narrow end of the rear panel (501). Accordingly, in one or more embodiments the narrow end of the inverse frustoconical shape has a width 604 of between two and four inches. For example, in one or more embodiments the narrow end of the inverse frustoconical shape has a width 604 of about three inches. These measurements are illustrative only, as others will be obvious to those of ordinary skill in the art having the benefit of this disclosure.

In one or more embodiments, the interior panel 601 is attached to the rear panel (501), which is attached to the drape 101. Accordingly, in such an embodiment the interior panel 601 is not directly attached to the drape 101.

The interior panel 601 can be coupled to the rear panel (501) in a variety of ways. In one or more embodiments, the interior panel 601 is attached to the rear panel (501) by thermal bonding. In another embodiment, the interior panel 601 is attached to the rear panel (501) by ultrasonic welding. In another embodiment, the interior panel 601 is attached to the rear panel (501) by an adhesive coupling. Other techniques for attaching the interior panel 601 is attached to the rear panel (501) will be obvious to those of ordinary skill in the art having the benefit of this disclosure.

In the illustrative embodiment of FIG. 6, the interior panel 601 is attached to the rear panel (501) by a perimeter seam 116. While referred to as a "perimeter" seam due to the fact that the perimeter seam 116 passes about the perimeter edge of the interior panel 601, note that the perimeter seam 116 does not pass around the entirety of the perimeter. Instead, as shown in FIG. 6, the perimeter seam 116 passes along three sides of the interior panel 601, thereby defining a closed end 607 of the pouch 605 defined by the interior panel 601, the rear panel (501), and the perimeter seam 116 (where the perimeter seam 116 is positioned), and an open end 606 positioned between the two terminal ends of the perimeter seam 116. In one or more embodiments, the perimeter seam 116 comprises a thermally bonded seam defining one or more closed sides between a pouch 605 defined by the interior panel 601, the rear panel (501) and the perimeter seam 116, as well as an open end of this pouch 605 where the interior panel 601 and the rear panel (501) are not bounded by the perimeter seam 116.

In the illustrative embodiment of FIG. 6, the interior panel 601, the rear panel (501), and the perimeter seam 116 define a first pouch 605 of the twin pouch assembly (102). Specifically, the wider, upper ends of the interior panel 601 and the rear panel (501) defines the open end (105) of this first pouch 605 of the twin pouch assembly (102), while the narrower, lower ends of the rear panel (501) and the interior panel 601, which are closed by a perimeter seam 116, define the body of the first pouch 605.

In one or more embodiments, the interior panel 601 is optically transparent so that fluids positioned within the first pouch 605 defined by the rear panel (501), the interior panel 601, and the perimeter seam 116 can be seen. Said differently, in one or more embodiments the interior panel 601 is pellucid, and forms a transparent interior barrier of the twin pouch assembly (102) separating the first pouch 605 from a second pouch that will be created when a front panel is attached to the interior panel 601 as described below with reference to FIG. 7. Illustrating by example, in one or more embodiments the interior panel 601 can be manufactured from 0.06-millimeter clear polyethylene so as to be translucent or pellucid. In one or more embodiments, the interior panel 601 is manufactured from clear 0.06 mm polyethylene sheeting. It should be noted that other clear, flexible materials may be used in place of polyethylene.

As noted, the perimeter seam 116, which passes along the perimeter of three of the four sides of the pouch 605 defined by the interior panel 601 and the rear panel (501) defines two opposing ends of this pouch 605. To wit, it creates an openable end 606 of the pouch 605 and a closed end 607 of the pouch 605. In FIG. 6, the pouch is shown in a flattened shape, with the openable end 606 in a closed position. By contrast, in FIGS. 13-14 described below, the openable end 606 of the pouch 605 will be shown in the open position.

In the illustrative embodiment of FIG. 6, the interior panel 601 defines a first major face 608 of the pouch 605, shown as the front face of the pouch 605 in FIG. 6. The rear panel (501) then defines a second major face, which would be the major face of the pouch 605 facing the drape 101 in FIG. 6. Side portions of the pouch 605 are then defined by the perimeter seam 116.

Figure 16:
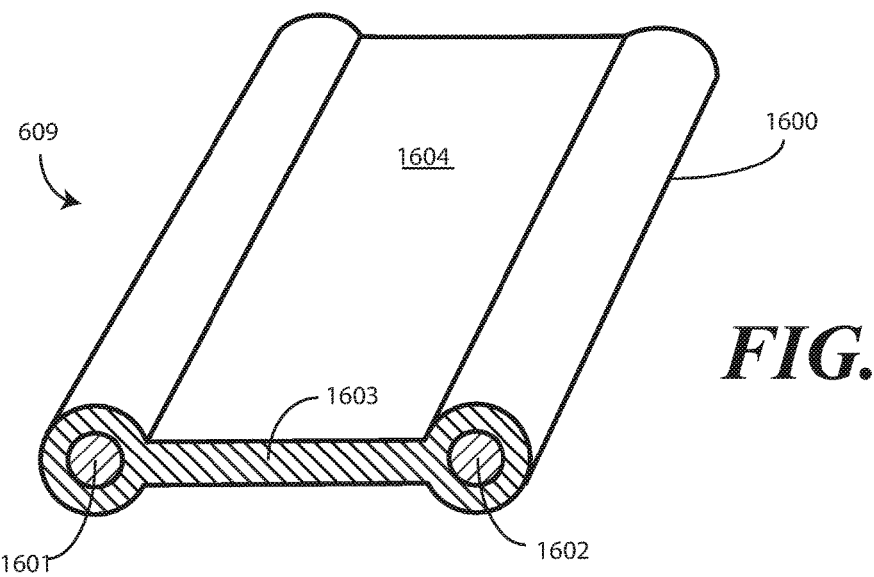
FIG. 16 illustrates one explanatory flexible strip suitable for attachment to a panel of a twin pouch assembly in accordance with one or more embodiments of the disclosure.

In one embodiment, a flexible strip 609 is attached to the first major face 608 of the first pouch 605. The flexible strip 609 can take a variety of forms. In one or more embodiments, the flexible strip 609 includes one or more wires or other bendable pieces of metal so as to be easily deformable to a desired shape. In one embodiment, the flexible strip 609 comprises a two-wire strip. While a two-wire strip will be used as an explanatory flexible strip 609 for illustrative purposes, it should be noted that the flexible strip 609 could include one wire, three wires, or more wires. Turning briefly to FIG. 16, illustrated therein is one example of such a two-wire strip 1600.

As shown in FIG. 16, in one embodiment the flexible strip 609 is a two-wire strip 1600 comprising two strands 1601, 1602 of flexible wire disposed within a thermoplastic binder 1603. In one embodiment, the flexible wire is a bendy wire manufactured from a malleable metal such as soft-annealed iron having a twenty-six or greater gauge measurement. Such wires are less than ten thousandths of an inch in diameter. Thicker wires can be used to stiffen the flexible strip 609. Moreover, in other embodiments the flexible strip 609 can be a single-wire strip, three-wire strip, four-wire strip, and so forth. In other embodiments, such as where the twin pouch assembly (102) will be subjected to radiation to kill microorganisms, bacteria, or pathogens, non-metallic malleable materials can be substituted for the wires described above. Still other configurations will be obvious to those of ordinary skill in the art having the benefit of this disclosure.

The thermoplastic binder 1603 can be made from a variety of materials. In one or more embodiments, the thermoplastic binder 1603 is manufactured from a flexible thermoplastic. Examples of flexible thermoplastics include polyvinyl materials, polystyrene, nylon, cellulose esters, and so forth. Polyethylene can also be used for the thermoplastic binder 1603. In one or more embodiments the material selected for use as the thermoplastic binder 1603 is one that securely bonds to the strands 1601,1602.

In one or more embodiments, the center 1604 of the two-wire strip 1600 can be textured. For example, it can include one or more bumps, protrusions, slits, or other surface features that assist a user in grasping the two-wire strip 1600 during a bending operation. Further, the thermoplastic binder v03 can be color-coded to indicate, for example, that the twin pouch assembly (102) is specifically designed as a parturition device, a medical waste device, or other type of bag.

In one or more embodiments, the two-wire strip 1600 is manufactured via an extrusion process. In one explanatory extrusion process, the strands 1601, 1602 are passed through an extruder that applies the thermoplastic binder 1603 about the strands 1601, 1602.

Turning now back to FIG. 6, in one embodiment the flexible strip 609 is adhesively disposed along the first major face 608 of the first pouch 605. In this illustrative embodiment, the flexible strip 609 is disposed on the first major face 608 of the first pouch 605 closer to the open end 606 than the closed end 607, as shown in FIG. 6.

In one embodiment, an adhesive strip 610 is also attached to the first major face 608 of the first pouch 605. In this illustrative embodiment, the adhesive strip 610 is disposed horizontally along the first major face 608 of the first pouch 605 as shown in FIG. 6. In one or more embodiments, the adhesive strip 610 comprises a double-sided adhesive tape having a vertical width of about two inches and a horizontal length of about twenty-four inches.

In one embodiment the adhesive strip 610 is initially covered with a releasable liner that is situated atop the adhesive strip 610. A user can remove the releasable liner to reveal the adhesive strip 610 so that the wider portion of the interior panel 601 can be attached to a front panel, as will be described below with reference to FIGS. 13-14. One or more labels 611 can be attached to the first major face 608 of the first pouch 605 instructing a user to remove the releasable liner from the adhesive strip 610 for this purpose.

It will be clear to those of ordinary skill in the art having the benefit of this disclosure that other coupling devices can be used for the adhesive strip 610. Examples include hook and loop fasteners, mechanical clasps, or other fasteners. The adhesive strip 610 need only be configured to attach the interior panel 601 to the front panel, as will be described below with reference to FIGS. 13-14.

In one embodiment, indicia are disposed on the one or more labels 611 instructing removal of the releasable liner. Illustrating by example, where the adhesive strip 610 comprises double-sided tape with a releasable liner, the one or more labels 611 may include the words "Peel Here," or other indicia instructing a user to remove the releasable liner from the adhesive strip 610. In other embodiments, the one or more labels 611 may include the words "remove liner" and two arrows. Other indicia can be included on the one or more labels 611 as well.

In the illustrative embodiment of FIG. 6, the flexible strip 609 and the adhesive strip 610 are disposed on the same major face 608 of the interior panel 601. In this embodiment, the flexible strip 609 is disposed closer to the open end 606 of the pouch 605, while the adhesive strip 610 is disposed farther from the open end 606 of the pouch 605. However, the opposite could be true, with the flexible strip 609 disposed closer to the open end 606 of the pouch 605, while the adhesive strip 610 is disposed farther from the open end 606 of the pouch 605. Further, both the flexible strip 609 and the adhesive strip 610 may be disposed on opposite major faces of the interior panel 601 in other embodiments. Other configurations will be obvious to those of ordinary skill in the art having the benefit of this disclosure.

In one or more embodiments, the flexible strip 609 and the adhesive strip 610 are disposed nearer to the open end 606 of the pouch 605 than the closed end 607, which is the end parallel to the open end 606. In one embodiment, the interior panel 601 defines a length 603 of the first pouch 605 and the flexible strip 609 and the adhesive strip 610 are disposed a distance of ten percent or less of the length 603 from the open end 606. In the illustrative embodiment of FIG. 6, the top of the flexible strip 609 and the top of the adhesive strip 610 are two inches or less from the open end 606, which is less than ten percent of the length 603 when the length 603 is about thirty-one inches.

In one embodiment, a width of the flexible strip 609 and a width of the adhesive strip 610 are each less than a width of the major faces of the first major face 608 of the first pouch 605 where they are attached. In one embodiment, the width of the adhesive strip 610 is the same as the width of the flexible strip 609. Other configurations will be obvious to those of ordinary skill in the art having the benefit of this disclosure.

Figure 13:
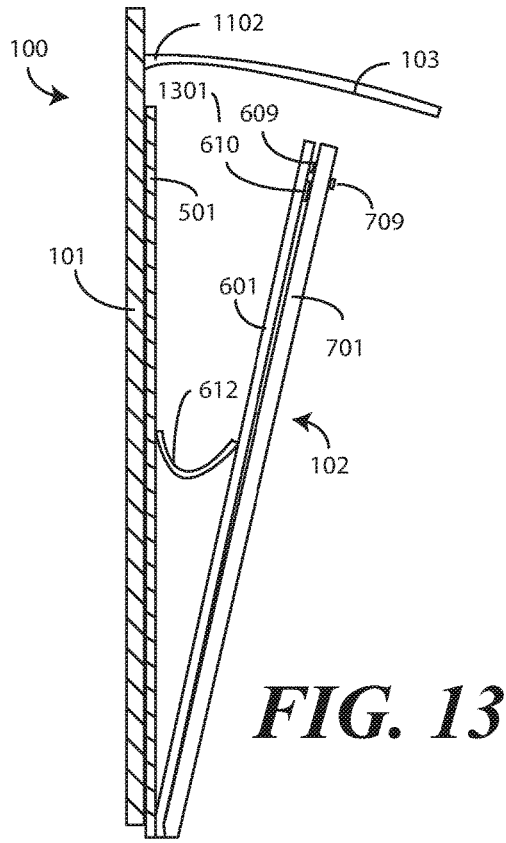
FIG. 13 illustrates a sectional view of one explanatory parturition drape in a third state of use in accordance with one or more embodiments of the disclosure.
Figure 14:
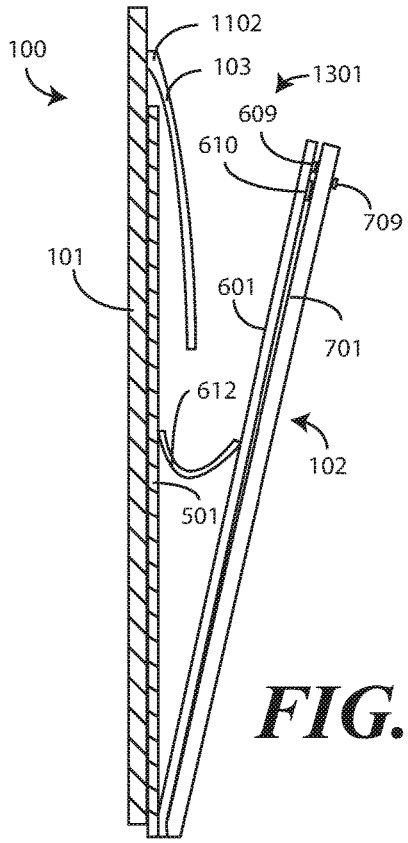
FIG. 14 illustrates a sectional view of one explanatory parturition drape in a fourth state of use in accordance with one or more embodiments of the disclosure.

In one or more embodiments, the flexible strip 609 is bendable to retain the open end 606 of the pouch 605 in an open position. This is shown in FIGS. 13-14. Illustrating by example, in one or more embodiments a user can bend the bendable and/or flexible strip 609 to retain the open end 606 of the pouch 605 in the open position. The inclusion of the bendable and/or flexible strip 609 is advantageous because the bendable and/or flexible strip 609 can retain the open end 606 of the pouch 605 in the open position regardless of whether the pouch 605 is positioned vertically or in another non-vertical orientation. Accordingly, when the drape 101 hangs from a surface, such as a table, bed, or other patient-supporting surface, the flexible strip 609 still retains the open end 606 of the pouch 605 in an open position.

When the pouch 605 is in the open position, the flexible strip 609 is malleable so as to be adjustable into different shapes. Accordingly, a user can bend the flexible strip 609 such that the open end 606 takes any of a variety of shapes, including semi-circular, angular, elliptical, or free form shapes.

In one or more embodiments, a sieve 612 is coupled between the interior panel 601 and the rear panel (501). In one or more embodiments, the sieve 612 works to catch and collect any tissue, non-liquids, instruments, sponges, or other medical implements that may fall through the open end 606 into the first pouch 605. The inclusion of the sieve 612, which is optional, allows such items to be retrieved prior to measuring any fluid that has accumulated in the first pouch 605. Advantageously, including the sieve 612 allows for a more accurate fluid measurement.

Figure 17:
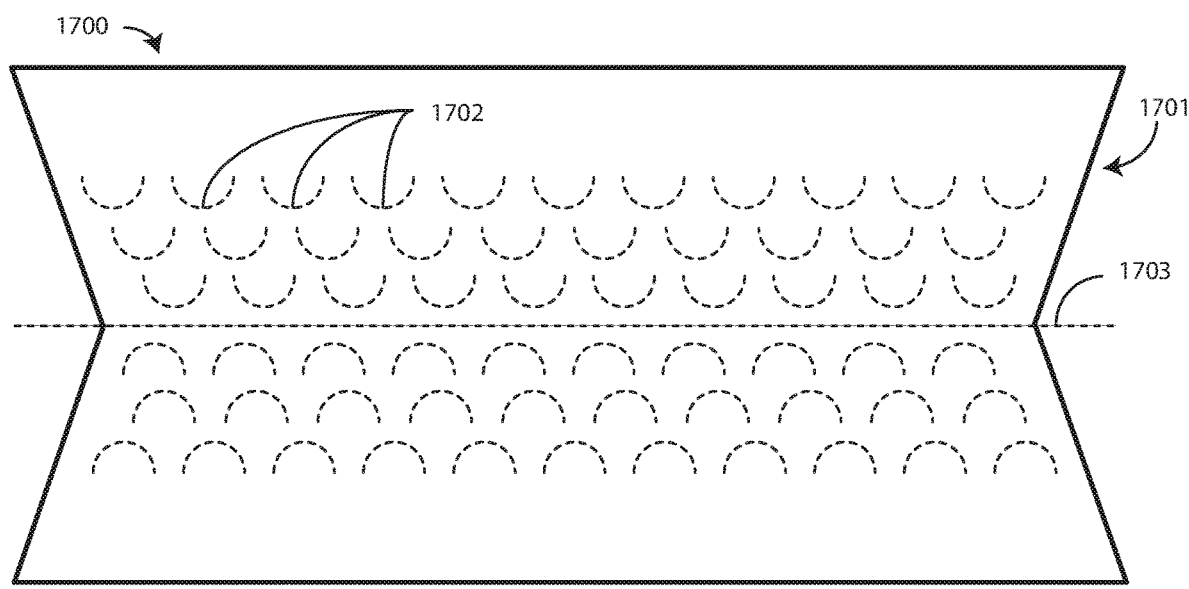
FIG. 17 illustrates one explanatory sieve suitable for attachment to a twin pouch assembly in accordance with one or more embodiments of the disclosure.

In one or more embodiments, the sieve 612 is coupled between the interior panel 601 and the rear panel (501) by the perimeter seam 116. Turning briefly to FIG. 17, illustrated therein is one explanatory sieve 1700 suitable for use as sieve 612 in FIG. 6. The sieve 1700 of FIG. 17 is also suitable for use as the sieve (118) of FIG. 1 as well.

As shown in FIG. 17, in this illustrative embodiment the sieve 1700 has a partially quadragrammatic shape 1701. While a quadrigram is a polygon with sides at opposite corners that cross, the sieve 1700 of FIG. 17 is partially quadragrammatic because it is effectively formed by two frustoconical shapes that abut at their small sides along a medial line 1703, thereby causing the shape of the sieve 1700 to be wider than a perfect quadrigram. This construction using two frustoconical shapes that abut at their small sides along a medial line 1703 allows the sieve 1700 to be folded along the medial line 1703 to define a double-layer inverse frustoconical sieve that can situate between panels of a twin pouch assembly (102) and be sealed therebetween by a perimeter seam (116).

In one or more embodiments, the sieve 1700 includes a plurality of perforations 1702 that allow liquids to pass therethrough while precluding the passage of large objects such as body tissues, surgical implements, sponges, and so forth. Illustrating by example, in one or more embodiments each perforation of the plurality of perforations is configured as one or more of slits or small holes that to allow the passage of fluids into the lower portions of the twin pouch assembly (102) while retaining solid objects within the upper portion of the twin pouch assembly (102).

In the illustrative embodiment of FIG. 17, the sieve 1700 is manufactured from clear polyethylene. For instance, in one or more embodiments the sieve 1700 is manufactured from a layer of clear 0.06 mm polyethylene sheeting. It should be noted that other clear, flexible materials may be used in place of polyethylene.

In the illustrative embodiment of FIG. 17, each perforation of the plurality of perforations 1702 comprises a semi-circular incision in the layer of polyethylene. The semicircular incisions create openings within the polyethylene sheeting that allow fluids to pass through the sieve 1700 while catching solid objects. While semicircular incisions are one technique by which the plurality of perforations 1702 can be constructed, others will be obvious to those of ordinary skill in the art having the benefit of this disclosure. Illustrating by example, in another embodiment the plurality of perforations 1702 are constructed by creating circular apertures in the layer of polyethylene. In still other embodiments, the plurality of perforations 1702 is constructed by creating linear incisions in the polyethylene, and so forth. In still other embodiments, netting or mesh can be used to construct the sieve 1700 rather than a sheet of polyethylene.

In one or more embodiments, folding the upper frustoconical shape relative to the lower frustoconical shape about the medial line 1703 allows the sieve 1700 to be expandable. Turning now back to FIG. 6, when, for example, the sieve (1700) of FIG. 17 is used as sieve 612 and is coupled between the interior panel 601 and the rear panel (501), the sieve 612 expands when the first pouch 605 is opened. It additionally collapses when the first pouch 605 is closed.

Figure 7:
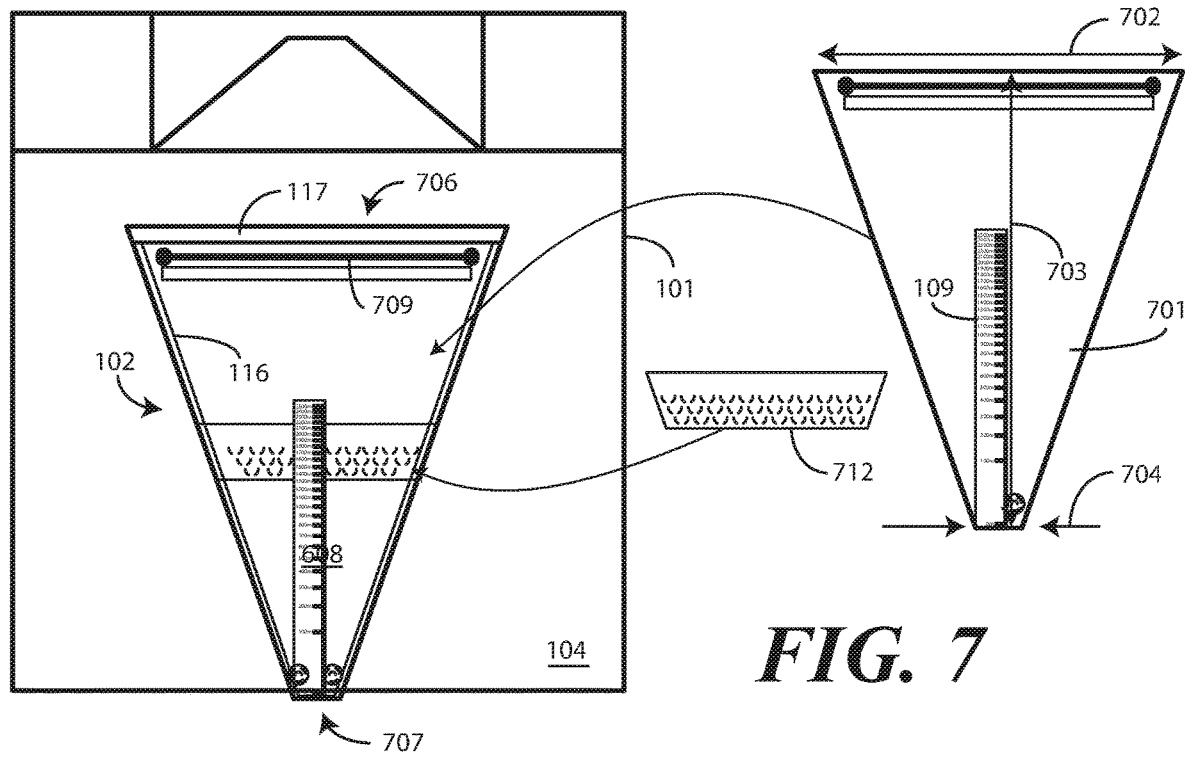
FIG. 7 illustrates another explanatory partially constructed parturition drape in accordance with one or more embodiments of the disclosure.

Turning now to FIG. 7, illustrated therein is a front panel 701 of a twin pouch assembly 102 being attached to the interior panel (601) to create a twin pouch assembly 102. In the illustrative embodiment of FIG. 7, the front panel 701 is attached to the interior panel (601) on a side of the interior panel (601) situated opposite the rear panel (501). This results in the interior panel (601) being positioned between the rear panel (501) and the front panel 701, thereby defining a first pouch (605) situated between the rear panel (501) and the interior panel (601) and a second pouch situated between the interior panel (601) and the front panel 701.

In this illustrative embodiment, the front panel 701 has an inverse frustoconical shape, as did the interior panel (601) and the rear panel (501). As with the interior panel (601) and the rear panel (501), while the front panel 701 is inverse frustoconical in this illustrative embodiment, it could take other shapes as well. For example, each of the rear panel (501), the interior panel (601), and the front panel 701 could be U-shaped, rectangularly shaped, triangularly shaped, or take other shapes. Still other possible shapes will be obvious to those of ordinary skill in the art having the benefit of this disclosure.

In one or more embodiments, the front panel 701 has a length 703 that is less than that of the rear panel (501), but is same as that of the interior panel (601). In one or more embodiments, the front panel 701 has a width 702 at its wide end that is narrower than the width (502) of the wide end of the rear panel (501), but that is the same as the width (602) of the wide end of the interior panel (601).

Illustrating by example, in one or more embodiments the wide end of the inverse frustoconical shape has a width 702 of between twenty-seven and twenty-nine inches. In one or more embodiments the wide end of the inverse frustoconical shape has a width 702 of about twenty-eight inches. In one or more embodiments, the length 703 of the inverse frustoconical shape is between thirty and thirty-two inches. In one or more embodiments the length 703 of the inverse frustoconical shape is about thirty inches.

These dimensions result in the rear panel (501) having an overall area that is greater than that of either the interior panel (601) or the front panel 701. At the same time, the interior panel (601) and the front panel 701 are coextensive in area. As before, since the wide end of the inverse frustoconical shape of the front panel 701 has a width 702 that is less than the width (502) of the wide end of the rear panel (501), this allows the extra length 117 of the rear panel (501) to be used for the adhesive coupling (505) to adhesively attach the twin pouch assembly 102 defined by the rear panel (501), the interior panel (601), the front panel 701, and the perimeter seam 116 to the first major surface 104 the drape 101 in one or more embodiments.

In one or more embodiments, since the front panel 701 has a narrow end having a width 704 that is the same as the narrow ends of the rear panel (501) and the interior panel (601), the narrow end of the twin pouch assembly 102 has that same width 704 as well. Accordingly, in one or more embodiments the narrow end of the twin pouch assembly 102 has a width 704 of between two and four inches. In one or more embodiments the narrow end of the twin pouch assembly 102 has a width 704 of about three inches. These measurements are illustrative only, as others will be obvious to those of ordinary skill in the art having the benefit of this disclosure.

In one or more embodiments, the front panel 701 is attached to the interior panel (601), which is then attached to the rear panel (501). In one or more embodiments, only the rear panel (501) is attached to the drape 101. Accordingly, in such an embodiment the front panel 701 is not directly attached to the drape 101. It, like the interior panel (601), is coupled to the drape 101 via the rear panel (501).

Like the interior panel (601), the front panel 701 can be coupled to the interior panel (601) in a variety of ways. In one or more embodiments, the front panel 701 is attached to the interior panel 601 by thermal bonding. In another embodiment, the front panel 701 is attached to the interior panel 601 by ultrasonic welding. In another embodiment, the front panel 701 is attached to the interior panel 601 by an adhesive coupling. Other techniques for attaching the front panel 701 to the interior panel (601) will be obvious to those of ordinary skill in the art having the benefit of this disclosure.

In the illustrative embodiment of FIG. 7, the front panel 701 is attached to the interior panel 601 by the perimeter seam 116 as previously described. This results in the perimeter seam 116 defining a closed end 707 of the twin pouch assembly 102 and an open end 706 of the twin pouch assembly 102 positioned between the two terminal ends of the perimeter seam 116. In one or more embodiments, the perimeter seam 116 comprises a thermally bonded seam defining one or more closed sides of the twin pouch assembly 102, as well as an open end 706 of the twin pouch assembly 102 where the rear panel (501), the interior panel (601), and the front panel 701 are unbounded by the perimeter seam 116.

In the illustrative embodiment of FIG. 7, the interior panel (601), the front panel 701, and the perimeter seam 116 define a second pouch of the twin pouch assembly 102, which is shown in the open position in FIGS. 11-12 below. Specifically, the wider, upper ends of the interior panel (601) and the front panel 701 define the open end of this second pouch of the twin pouch assembly 102, while the narrower, lower ends of the interior panel (601) and the front panel 701, which are closed by a perimeter seam 116, define the body of the second pouch.

In one or more embodiments, the front panel 701 is optically transparent so that fluids positioned within the second pouch defined by the front panel 701, the interior panel (601), and the perimeter seam 116 can be seen. Said differently, in one or more embodiments the front panel 701 is pellucid, and forms a transparent interior barrier of the twin pouch assembly 102 bounding the exterior of the first pouch. Illustrating by example, in one or more embodiments the front panel 701 can be manufactured from 0.06-millimeter clear polyethylene so as to be translucent or pellucid. In one or more embodiments, the front panel 701 manufactured from clear 0.06 mm polyethylene sheeting. It should be noted that other clear, flexible materials may be used in place of polyethylene.

In the illustrative embodiment of FIG. 7, the front panel 701 defines a first major face of the pouch defined by the front panel 701, the interior panel (601), and the perimeter seam 116. The interior panel (601) then defines a second major face of the pouch defined by the front panel 701, the interior panel (601), and the perimeter seam 116. Side portions of the pouch are then defined by the perimeter seam 116.

In one embodiment, another flexible strip 709 is attached to the first major face of the second pouch. In this illustrative embodiment, the flexible strip 709 is attached to the exterior surface of the front panel 701. The other flexible strip 709 is configured to retain the second pouch defined by the front panel 701, the interior panel (601), and the perimeter seam 116 in the open position. When a flap (103) is attached to the first major surface 104 of the drape 101, the other flexible strip 709 is configured to retain the second pouch in the open position when the flap (103) is inserted into the second pouch.

As with the flexible strip (609) of FIG. 6, in one or more embodiments the flexible strip 709 includes one or more wires or other bendable pieces of metal so as to be easily deformable to a desired shape. In one embodiment, the flexible strip 709 comprises a two-wire strip. It should be noted that the flexible strip 709 could include one wire, three wires, or more wires. One explanatory two-wire strip (1600) suitable for use as the flexible strip 709 was described above with reference to FIG. 16. Others will be obvious to those of ordinary skill in the art having the benefit of this disclosure.

In one or more embodiments, the flexible strip 709 is adhesively disposed along the exterior major face of the second pouch. In this illustrative embodiment, the flexible strip 709 is disposed on the first major face of the second pouch closer to the open end 706 than the closed end 707. When the second pouch is in the open position, the flexible strip 709 is malleable so as to be adjustable into different shapes that retain the second pouch in the open position. Accordingly, a user can bend the flexible strip 709 such that the open end 706 takes any of a variety of shapes, including semi-circular, angular, elliptical, or free form shapes.

In one or more embodiments, another sieve 712 is coupled between the interior panel (601) and the front panel 701. As before, where included the sieve 712 works to catch and collect any tissue, non-liquids, instruments, sponges, or other medical implements that may fall through the open end 706 into the second pouch. The inclusion of the sieve 712, which is optional, allows such items to be retrieved prior to measuring any fluid that has accumulated in the second pouch. Advantageously, including the sieve 712 allows for a more accurate fluid measurement. In one or more embodiments, the sieve 712 is coupled between the interior panel (601) and the front panel 701 by the perimeter seam 116.

In one or more embodiments, a graduated fluid measurement device 109 is positioned on an exterior surface of the front panel 701. In one or more embodiments, the graduated fluid measurement device 109 indicates a volume of fluid situated in the first pouch of the twin pouch assembly 102. In one or more embodiments, where each of the front panel 701, the interior panel (601), and the rear panel (501) are pellucid, their transparency allows the graduated fluid measurement device 109 to be used to measure the amount of fluid in the first pouch (605) of the twin pouch assembly 102 as well. Advantageously, this graduated fluid measurement device 109, when used in conjunction with the twin pouch assembly 102, allows a health care services provider to accurately measure both amniotic fluid guided into one of the first pouch or the second pouch of the twin pouch assembly 102 and blood and/or placenta fluids guided into another of the first pouch or the second pouch of the twin pouch assembly 102.

In one or more embodiments, the graduated fluid measurement device 109 comprises graduations that measure fluids disposed within the first pouch and/or second pouch in milliliters. Illustrating by example, in one embodiment the graduated fluid measurement device 109 comprises graduations and corresponding indicators that commence at a first graduation and indicator indicating one hundred milliliters. In one or more embodiments, the graduations then increase in 100-ml increments and terminate at a final graduation and indicator indicating 2500 milliliters. These measurements are well suited for obstetric procedures, although others will be obvious to those of ordinary skill in the art having the benefit of this disclosure.

Figure 8:
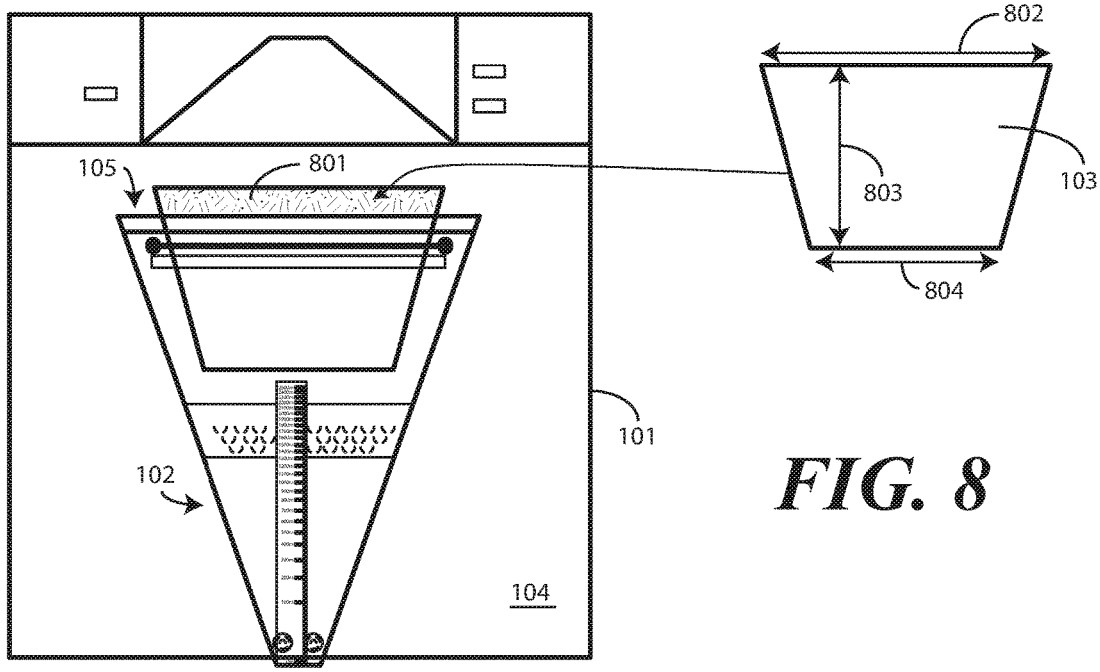
FIG. 8 illustrates another explanatory partially constructed parturition drape in accordance with one or more embodiments of the disclosure.

Turning now to FIG. 8, a flap 103 is being attached to the first major surface 104 of the drape 101. In one or more embodiments, the flap 103 is selectively insertable into an open end 105 of either the first pouch or the second pouch of the twin pouch assembly 102 so as to guide fluids passing down the major surface 104 of the drape 101 into the first pouch or second pouch as desired.

In one or more embodiments, the flap 103 is opaque. In one or more embodiments, the flap 103 comprises a layer of material that is generally water resistant or waterproof. In one or more embodiments, the flap 103 comprises a single layer of material.

In one or more embodiments, the flap 103 is manufactured from the same material is the drape 101. Accordingly, in one or more embodiments the flap 103 is manufactured from a single layer of polyethylene or polyurethane. Illustrating by example, in one or more embodiments the flap is manufactured from 0.065 millimeter, blue polyethylene. In other embodiments, the flap 103 can be a multi-ply layer of material. Other materials suitable for use as the flap 103 will be obvious to those of ordinary skill in the art having the benefit of this disclosure. For instance, in other embodiments the flap 103 is pellucid.

The flap 103 can be attached to the first major surface 104 of the drape 101 in a variety of ways. In one or more embodiments, the flap 103 is attached to the drape 101 by thermal bonding. In another embodiment, the flap 103 is attached to the drape 101 by ultrasonic welding. In the illustrative embodiment of FIG. 8, the flap 103 is attached to the first major surface 104 of the drape 101 by an adhesive coupling 801. Other techniques for coupling the flap 103 to the first major surface 104 of the drape 101 will be obvious to those of ordinary skill in the art having the benefit of this disclosure.

In this illustrative embodiment, the flap 103 has an inverse frustoconical shape. However, in other embodiments it could take other shapes as well. For example, the flap 103 could be U-shaped, rectangularly shaped, triangularly shaped, or take other shapes. Still other possible shapes will be obvious to those of ordinary skill in the art having the benefit of this disclosure.

In one or more embodiments, the flap 103 has a length 803 that is less than that of the twin pouch assembly 102. In one or more embodiments, the front panel 701 has a width 802 at its wide end that is narrower than that of the twin pouch assembly 102.

Illustrating by example, in one or more embodiments the wide end of the inverse frustoconical shape has a width 802 of between nineteen and twenty-one inches. In one or more embodiments the wide end of the inverse frustoconical shape has a width 802 of about twenty inches. In one or more embodiments, the length 803 of the inverse frustoconical shape is between eleven and thirteen inches. In one or more embodiments the length 803 of the inverse frustoconical shape is about twelve inches.

In one or more embodiments, so as to be insertable into the open end of either the first pouch or the second pouch of the twin pouch assembly 102, the flap 103 has a narrow end with a width 804 that is between eleven and thirteen inches.

In one or more embodiments the narrow end of the flap 103 has a width 804 of about twelve inches. These measurements are illustrative only, as others will be obvious to those of ordinary skill in the art having the benefit of this disclosure.

These dimensions result in the flap 103 having an overall area that is less than that of the twin pouch assembly 102. Since the wide end of the inverse frustoconical shape of the flap 103 has a width 802 that is less than that of the twin pouch assembly 102, this allows the flap 103 to insert into the open end of either the first pouch or the second pouch of the twin pouch assembly 102 as desired. In one or more embodiments, the wide end of the flap 103 is attached to the first major surface 104 of the drape 101 about three inches above the wide end of the front panel (701) and the interior panel (601), and about two inches above the wide end of the rear panel (501).

When viewed collectively, FIGS. 2-8 illustrated a method of manufacturing a parturition drape in accordance with one or more embodiments of the disclosure. Illustrating by example, FIGS. 5-7 illustrate one or more method steps for coupling a twin pouch assembly 102 defining a first pouch and a second, adjacent, coextensive pouch to a first major surface 104 of a drape 101. This occurs, in one or more embodiments, by coupling rear panel 501 to the first major surface 104 of the drape 101 with an interior panel 601 coupled by a perimeter seam 116 between a front panel 701 that is coextensive with the interior panel 601 and the rear panel 501 so as to define a first pouch between the rear panel 501 and the interior panel 601, and a second pouch between the interior panel 601 and the front panel 701. FIG. 8 then illustrates one or more method steps for coupling a flap 103 to the first major surface 104 of the drape 101. In one or more embodiments, as will be shown below with reference to FIGS. 11-14, the flap 103 is selectively insertable into either the first pouch or the second pouch, which is adjacent to, and coextensive with, the first pouch.

FIG. 7 illustrates one or more method steps for attaching a first flexible strip 709 to an outer surface of an outer panel, i.e., front panel 701, of the twin pouch assembly 102. FIG. 6 illustrates one or more method steps for attaching another flexible strip 609 to an outer surface of an interior panel 601 of the twin pouch assembly 102. FIG. 6 also illustrates one or more method steps for attaching an adhesive strip 610 that is configured to adhesively couple the outer surface of the interior panel 601 to the interior surface of the front panel while the flap 103 is inserted into an open end of the second pouch. While shown coupled to the exterior surface of the interior panel in FIG. 6, the adhesive strip 610 could be coupled to the interior surface of the front panel 701 in other embodiments.

Figure 9:
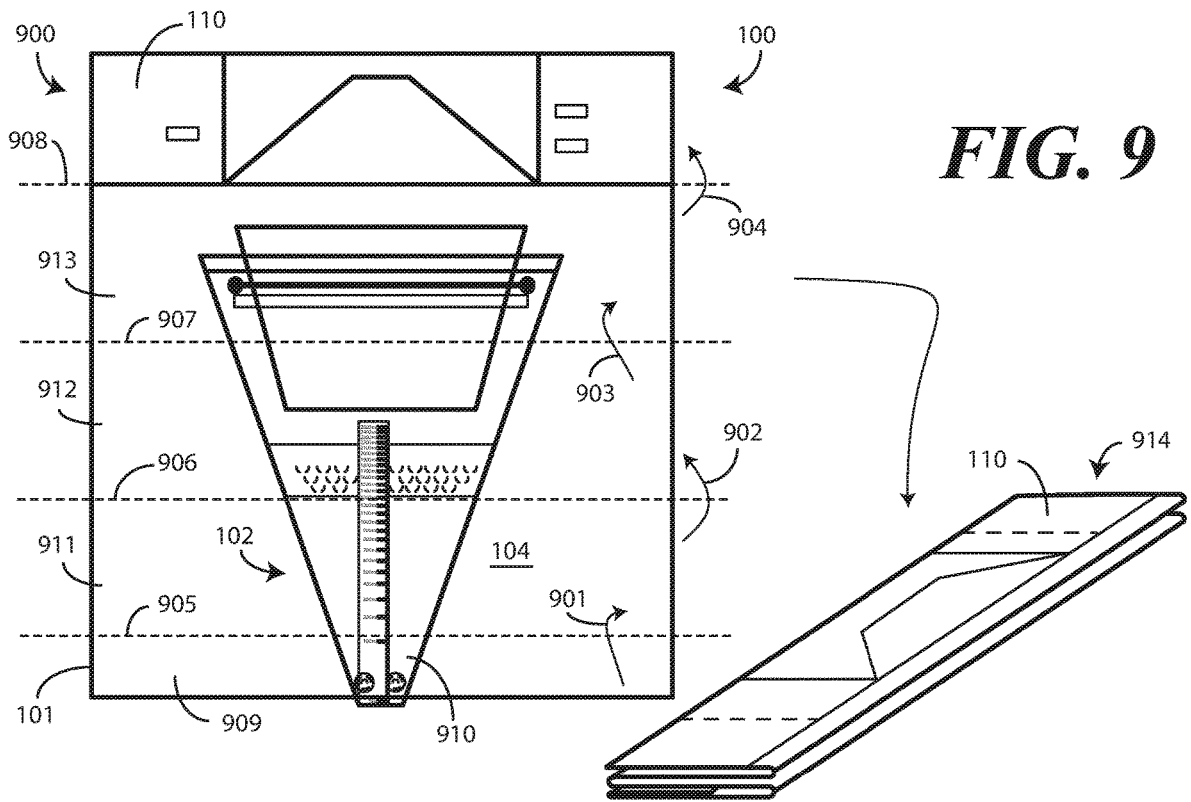
FIG. 9 illustrates one or more explanatory methods steps for folding an explanatory parturition drape in accordance with one or more embodiments of the disclosure.

Turning now to FIG. 9, illustrated therein is the parturition drape 100 that results from the one or more method steps of FIGS. 2-8. While shown as being flexible due to the fact that the rear panel (501), interior panel (601), and front panel (701) are manufactured from transparent polyethylene sheets in one or more embodiments, it should be noted that the twin pouch assembly 102 may alternatively be manufactured from rigid or semi-rigid materials as well. One advantage of using flexible materials for the twin pouch assembly 102 is that it allows for the twin pouch assembly 102 to be folded for easier storage and deployment, as shown in FIGS. 9-10.

Prior to folding, the parturition drape 100 of FIG. 9 is shown in an unfolded state 900. In one or more embodiments, the parturition drape 100 is then folded with four book folds. A first book fold 901, by which fold line 905 recedes downward and into the page, folds the base section 909 of the drape 101 and the bottom tip 910 of the twin pouch assembly 102 atop a second section 911 of the drape 101 such that the base section 909 and the second section 911, and corresponding portions of the twin pouch assembly 102, abut along the first major surface 104 of the drape 101.

A second book fold 902, which causes fold line 906 to rise outwardly from the page, causes the second section 911 of the drape 101 and a third section 912 of the drape 101 to abut along the rear major surface (115) of the drape 101. In one or more embodiments, this second book fold causes the base section 909 and the second section 911 to fold beneath the third section 912 of the drape 101.

A third book fold 903, which causes fold line 907 to move into the page, then causes the third section 912 and a fourth portion 913 of the drape 101 to abut along the first major surface 104 of the drape 101. A fourth book fold 904, causing fold line 908 to move out of the page causes the portion of the drape 101 defining the cuff 110 to abut the fourth portion 913 of the drape along the rear major surface (115) of the drape. The resulting partially folded drape 914 is shown in perspective view in FIG. 9, with the cuff 110 situated atop the partially folded drape 914.

Turning now to FIG. 10, the partially folded drape 914 can again be folded by five additional book folds to create a folded drape 1000. In one or more embodiments, the folding occurring in FIG. 10 allows a first cuff portion 1001 to be exposed on the right side 1003 of the folded drape 1000, and a second cuff portion 1002 to be exposed on the left side 1004 of the folded drape 1000. When deploying the drape, a health care services provider can insert a right hand into the first cuff portion 1001 and a left hand into the second cuff portion 1002. The health care services provider can then expand the folded drape 1000 by separating the first cuff portion 1001 from the second cuff portion 1002, thereby reversing the folding steps occurring in FIG. 10 and causing the folded drape 1000 to return to the partially folded drape 914 of FIG. 9. The health care services provider can then, while the right hand remains in the first cuff portion 1001 and the left hand remains in the second cuff portion 1002, extend the partially folded drape 914 to expose the parturition drape (100) of FIG. 1 without compromising the sterile field.

In one or more embodiments, the partially folded drape 914 is first folded with a first book fold 1005 and a second book fold 1006, each of which causes a first fold line 1007 and a second fold line 1008 to rise (as viewed in FIG. 10). This allows a first end portion 1009 and a second end portion 1010 to fold beneath the partially folded drape 914.

From there a third book fold 1011 and a fourth book fold 1012 cause a third fold line 1013 and a fourth fold line 1014 to rise. The third book fold 1011 about the third fold line 1013 causes the undersides of a first interior portion 1015 and a second interior portion 1017 to abut. The fourth book fold 1012 about the fourth fold line 1014 causes the undersides of a third interior portion 1016 and a fourth interior portion 1018 to abut. A final book fold 1019 about a final fold line 1020 causes the upper sides of the second interior portion 1017 and the fourth interior portion 1018 to abut, thereby created in the folded drape 1000.

Turning now to FIGS. 11-14, illustrated therein are sectional views of one explanatory parturition drape 100 in use. As previously described, the parturition drape 100 of FIGS. 11-14 includes a drape 101 and a twin pouch assembly 102. The twin pouch assembly 102 includes a rear panel 501 attached to a major face of the drape 101, a front panel 701 attached to the rear panel 501 by a perimeter seam (116), and an interior panel 601 positioned between the front panel 701 and the rear panel 501, thereby defining the twin pouch assembly 102. In the illustrative embodiments of FIGS. 11-14, the twin pouch assembly 102 comprises a first pouch 1101 and a second pouch 1301, each of which is coupled to the major face of the drape 101. In the illustrative embodiments of FIGS. 11-14, the front panel 701 and the interior panel 601 are coextensive in area, and thus constitute coextensive panels.

A flap 103 is also attached to the major face of the drape 101. In the illustrative embodiments of FIGS. 11-14, the flap 103 is attached to the major face of the drape 101 along a first edge 1102 of the flap 103. As best seen in FIGS. 11 and 14, in one or more embodiments the flap 103 is selectively insertable into an open end of either the first pouch 1101 or the second pouch 1301.

In one or more embodiments, a flexible strip 709 is attached to an exterior of the front panel 701. In the illustrative embodiments of FIGS. 11-14, another flexible strip 609 is attached to an exterior of the interior panel 601.

As shown in FIGS. 11-14, the flexible strip 709 is bendable and configured to retain the first pouch 1101 in an open position. As shown in FIG. 11, in one or more embodiments the flexible strip 709 is configured to retain the first pouch 1101 in the open position while the flap 103 is inserted into the first pouch 1101.

As shown in FIGS. 13-14, the other flexible strip 609 is bendable and configured to retain the sp 1301 in the open position. As shown in FIG. 14, in one or more embodiments the other flexible strip 609 is configured to retain the second pouch 1301 in the open position while the flap 103 is inserted into the second pouch 1301.

In one or more embodiments, an adhesive strip 610 is attached to an exterior of the interior panel 601. In one or more embodiments, the adhesive strip 610 is configured to adhesively couple the exterior of the interior panel 601 to the interior of the front panel 701. As shown in FIG. 14, in one or more embodiments the adhesive strip 610 is configured to adhesively couple the interior panel 601 to the interior of the front panel 701 when the flap 103 is inserted into the second pouch 1301.

Beginning with FIG. 11, when using the parturition drape 100 one initially unfolds the parturition drape 100 while maintaining the sterile field a described above with reference to FIGS. 9-10. A patient can then be placed atop the cuff (110). In one or more embodiments, the patient is placed upon the reinforcing material (113) for added stability and/or comfort. The parturition drape 100 is preferably placed near the edge of a table, bed, or other surface such that the portion of the drape 101 with the twin pouch assembly 102 hands down from the edge. Illustrating by example, the cuff (110) may be placed on the edge of a delivery table, while the portion of the drape 101 to which the twin pouch assembly 102 is attached hangs down vertically.

Thereafter, the front panel 701 is pulled away from the interior panel 601 while the flap 103 is inserted into the first pouch 1101. This opens the first pouch 1101. The flexible strip 709 can be bent and positioned to retain the first pouch 1101 in the open position while the flap 103 inserted into the first pouch 1101. While having the twin pouch assembly 102 hang vertically is preferred, it is not mandatory. The inclusion of the flexible strip 709 advantageously retains the first pouch 1101 in the open position regardless of whether the twin pouch assembly 102 is positioned horizontally or vertically.

When the first pouch 1101 is in the open position of FIG. 11, the flexible strip 609 is malleable so as to be adjustable into different shapes. Accordingly, a user can bend the flexible strip 609 such that the open end of the first pouch 1101 takes any of a variety of shapes, including semicircular, angular, elliptical, or free form shapes.

After the amniotic sac is punctured or ruptured, amniotic fluids can pass down the flap 103 into the first pouch 1101. These fluids pass through the optional sieve 712. They can then be measured using the graduated fluid measurement device (109).

Thereafter, as shown in FIG. 12, the flap 103 can be lifted from the first pouch 1101. A releasable liner 1201 can then be removed from the adhesive strip 610. The interior panel 601 is pulled away from the rear panel 501 while the flap 103 is removed from the first pouch 1101, as shown in FIG. 13. This opens the second pouch 1301. The flexible strip 609 can be bent and positioned to retain the second pouch 1301 in the open position. Additionally, the adhesive strip 610 can attach the interior panel 601 to the front panel 701 as previously described.

The flap 103 can then be inserted into the second pouch 1301 as shown in FIG. 12. Blood can then pass along the flap 103 into the second pouch 1301, through the optional sieve 612, where it can be measured using the graduated fluid measurement device (109). Either the amniotic fluid or blood can be drained using the drains (119,120) as previously described.

Figure 15:
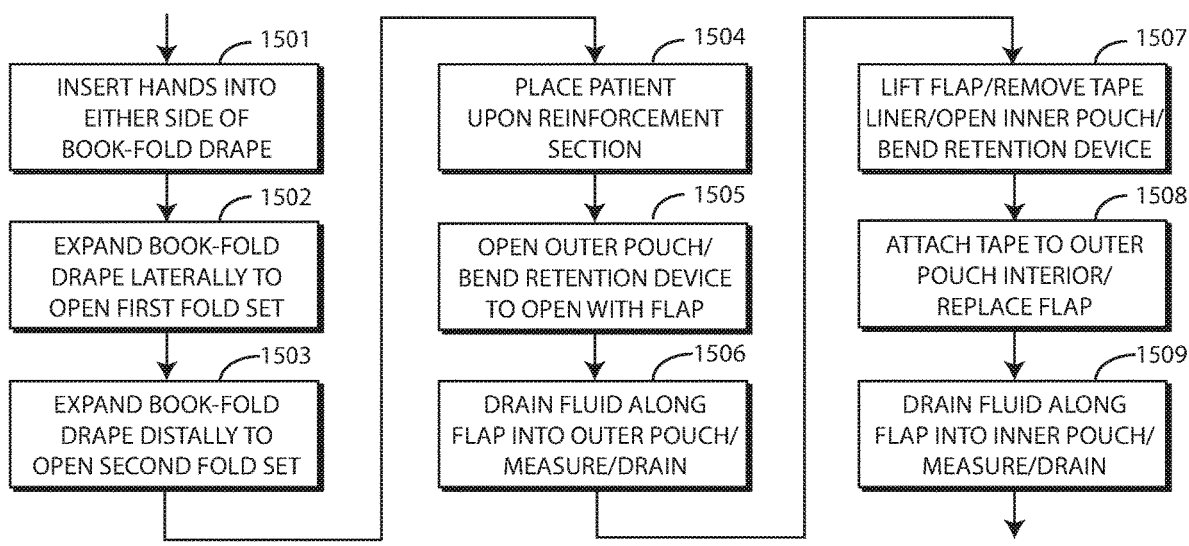
FIG. 15 illustrates one explanatory method for using a parturition drape in accordance with one or more embodiments of the disclosure.

Turning now to FIG. 15, this method 1500 of using the drape is summarized in a flow chart. Beginning at step 1501, a health care services provider first inserts their hands into the right side cuff and left side cuff of a folded drape. At step 1502, the health care services provider expands one or more book folds to transition the folded drape to a partially folded drape. At step 1503, the health care services provider expands one or more additional book folds to expand the partially folded drape to expose the full parturition drape.

At step 1504, the health care services provider places a patient atop the cuff of the parturition drape. In one or more embodiments, this comprises positioning a patient atop a reinforcing panel attached to the rear major face of the drape. In one or more embodiments, the reinforcing panel comprises a frustoconical recess facing the twin pouch assembly of the parturition drape.

At step 1505, the health care services provider opens a first pouch by pulling away a front panel from an interior panel of the twin pouch assembly. In one or more embodiments, this step 1505 includes bending a flexible strip to retain the first pouch in the open position while a flap attached to the drape above the twin pouch assembly inserts into the first pouch. Amniotic fluid can be drained into the first pouch at step 1506. Step 1506 can include measuring the amount of amniotic fluid using a graduated fluid measurement device positioned along the front panel as well in one or more embodiments.

At step 1507, the health care services provider removes the flap from the first pouch and pulls the interior panel of the twin pouch assembly away from a rear panel of the twin pouch assembly, thereby opening a second pouch. In one or more embodiments, step 1507 comprises bending another flexible strip to retain the second pouch in an open position. Step 1507 can optionally include removing a releasable layer from an adhesive strip attached to one of an exterior of the interior panel or an interior of the front panel.

Step 1508 comprises inserting the flap into the second pouch. Step 1508 can optionally include using the adhesive strip to attach the interior panel to the front panel. Blood can be drained into the second pouch at step 1509. Step 1509 can include measuring the amount of blood using a graduated fluid measurement device positioned along the front panel as well in one or more embodiments.

Figure 18:
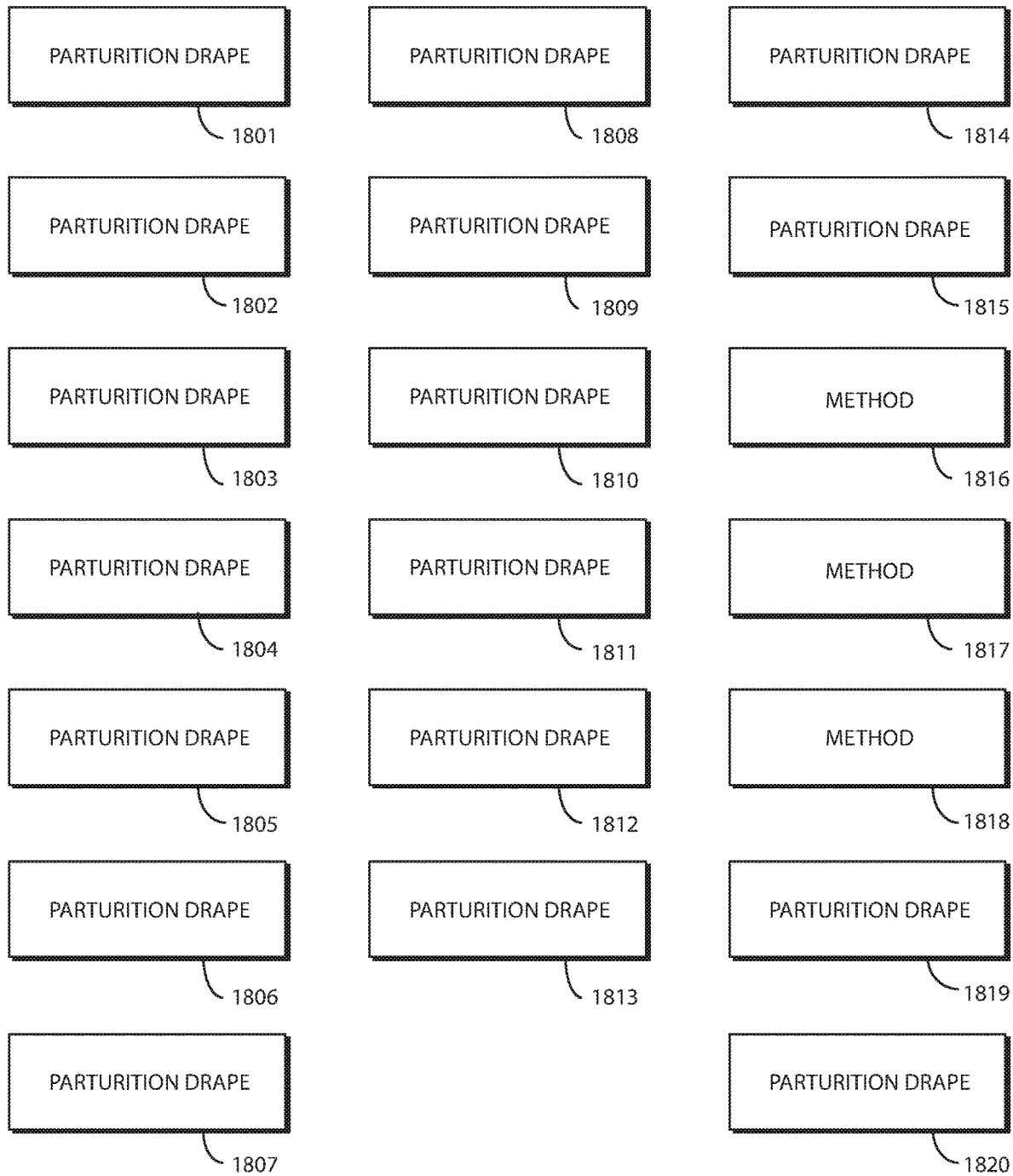
FIG. 18 illustrates various embodiments of the disclosure.

Turning now to FIG. 18, illustrated therein are various embodiments of the disclosure. The embodiments of FIG. 18 are shown as labeled boxes in FIG. 18 due to the fact that the individual components of these embodiments have been illustrated in detail in FIGS. 1-17, which precede FIG. 18. Accordingly, since these items have previously been illustrated and described, their repeated illustration is no longer essential for a proper understanding of these embodiments. Thus, the embodiments are shown as labeled boxes.

At 1801, a parturition drape comprises a drape and a twin pouch assembly. At 1801, the twin pouch assembly defines a first pouch and a second pouch attached to a major face of the drape. At 1801, a flap is also attached to the major face of the drape. At 1801, the flap is selectively insertable into an open end of either the first pouch or the second pouch.

At 1802, the twin pouch assembly of 1801 comprises a rear panel, an interior panel, and a front panel. At 1802, the rear panel, the interior panel, and the front panel are joined together by a perimeter seam.

At 1803, each of the rear panel, the interior panel, and the front panel of 1802 have an inverted frustoconical shape. At 1804, the parturition drape of 1803 further comprises a first sieve coupled between the rear panel and the interior panel by the perimeter seam.

At 1804, the flap of 1803 also has the inverted frustoconical shape. At 1806, the front panel, the interior panel, and the rear panel of 1805 are pellucid. At 1807, the flap of 1806 is opaque.

At 1808, the rear panel of 1802 has a length that is greater than that of the interior panel or the front panel. At 1808, the interior panel and the front panel are coextensive in area.

At 1809, the parturition drape of 1802 further comprises a flexible strip attached to an exterior of the front panel. At 1809, the flexible strip is configured to retain the first pouch in an open position while the flap is inserted into the first pouch.

At 1810, the parturition drape of 1809 further comprises another flexible strip attached to an exterior of the interior panel. At 1810, the other flexible strip is configured to retain the second pouch in the open position while the flap is inserted into the second pouch.

At 1811, the parturition drape of 1810 further comprises an adhesive strip attached to the exterior of the interior panel. At 1811, the adhesive strip is configured to adhesively couple the exterior of the interior panel to an interior of the front panel while the flap is inserted into the second pouch.

At 1812, the parturition drape of 1811 further comprises a graduated fluid measurement indicating a volume of fluid in both the first pouch and the second pouch positioned on the exterior of the front panel. At 1813, the drape of 1812 is folded along an edge with a first portion of the front major face abutting a second portion of the front major face, thereby defining a cuff positioned along the edge of the drape.

At 1814, the parturition drape of 1813 further comprises a reinforcing panel attached to a rear major face of the drape atop the cuff. At 1815, the reinforcing panel of 1814 defines a frustoconical recess facing the twin pouch assembly.

At 1816, a method of constructing a parturition drape comprises coupling a twin pouch assembly defining a first pouch and a second, adjacent, coextensive pouch to a first major face of a drape. At 1816, the method comprises coupling a flap to the first major face of the drape that is selectively insertable into an open end of either the first pouch or the second, adjacent, coextensive pouch.

At 1817, the method of 1816 further comprises attaching a first flexible strip to an outer surface of an outer panel of the twin pouch assembly and a second flexible strip to an outer surface of an interior panel of the twin pouch assembly. At 1818, the method of 1817 further comprises attaching an adhesive strip to the outer surface of the interior panel that is configured to adhesively couple the outer surface of the interior panel to an inner surface of the outer panel while the flap is inserted into an open end of the second pouch.

At 1918, a parturition drape comprises a drape. At 1819, the parturition drape comprises a rear panel attached to a major face of the drape, a front panel attached to the rear panel by a perimeter seam, and an interior panel positioned between the front panel and the rear panel, thereby defining a twin pouch assembly comprising a first pouch and a second pouch attached to a major face of the drape. At 1918, the parturition drape comprises a flap attached to the major face of the drape along a first edge of the flap.

At 1819, a second edge of the flap is selectively insertable into an open end of either the first pouch or the second pouch. At 1820, the front panel and the interior panel of 1819 are coextensive panels.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A parturition drape, comprising:
   a drape;
   a twin pouch assembly defining a first pouch and a second pouch attached to a major face of the drape; and
   a flap attached to the major face of the drape;
   wherein the flap is selectively insertable into an open end of either the first pouch or the second pouch.

2. The parturition drape of claim 1, wherein the twin pouch assembly comprises a rear panel, interior panel, and front panel joined together by a perimeter seam.

3. The parturition drape of claim 2, wherein each of the rear panel, the interior panel, and the front panel have an inverted frustoconical shape.

4. The parturition drape of claim 3, further comprising a first sieve coupled between the rear panel and the interior panel by the perimeter seam.

5. The parturition drape of claim 3, wherein the flap also has the inverted frustoconical shape.

6. The parturition drape of claim 5, wherein the front panel, the interior panel, and the rear panel are pellucid.

7. The parturition drape of claim 6, wherein the flap is opaque.

8. The parturition drape of claim 2, wherein the rear panel has a length greater than the interior panel or the front panel, further wherein the interior panel and front panel are coextensive.

9. The parturition drape of claim 2, further comprising a flexible strip attached to an exterior of the front panel, the flexible strip configured to retain the first pouch in an open position while the flap is inserted into the first pouch.

10. The parturition drape of claim 9, further comprising another flexible strip attached to an exterior of the interior panel, the another flexible strip configured to retain the second pouch in the open position while the flap is inserted into the second pouch.

11. The parturition drape of claim 10, further comprising an adhesive strip attached to the exterior of the interior panel configured to adhesively couple the exterior of the interior panel to an interior of the front panel while the flap is inserted into the second pouch.

12. The parturition drape of claim 11, further comprising a graduated fluid measurement indicating a volume of fluid in both the first pouch and the second pouch positioned on the exterior of the front panel.

13. The parturition drape of claim 12, wherein the drape is folded along an edge with a first portion of the major face abutting a second portion of the major face, thereby defining a cuff positioned along the edge of the drape.

14. The parturition drape of claim 13, further comprising a reinforcing panel attached to a rear major face of the drape atop the cuff.

15. The parturition drape of claim 14, wherein the reinforcing panel defines a frustoconical recess facing the twin pouch assembly.

16. A method of constructing a parturition drape, the method comprising:
    coupling a twin pouch assembly defining a first pouch and a second, adjacent, coextensive pouch to a first major face of a drape; and
    coupling a flap to the first major face of the drape that is selectively insertable into an open end of either the first pouch or the second, adjacent, coextensive pouch.

17. The method of claim 16, further comprising attaching a first flexible strip to an outer surface of an outer panel of the twin pouch assembly and a second flexible strip to an outer surface of an interior panel of the twin pouch assembly.

18. The method of claim 17, further comprising attaching an adhesive strip to the outer surface of the interior panel that is configured to adhesively couple the outer surface of the interior panel to an inner surface of the outer panel while the flap is inserted into an open end of the second, adjacent, coextensive pouch.

19. A parturition drape, comprising:
    a drape;
    a rear panel attached to a major face of the drape, a front panel attached to the rear panel by a perimeter seam, and an interior panel positioned between the front panel and the rear panel, thereby defining a twin pouch assembly comprising a first pouch and a second pouch attached to the major surface of the drape; and
    a flap attached to the major face of the drape along a first edge of the flap;
    wherein a second edge of the flap is selectively insertable into an open end of either the first pouch or the second pouch.

20. The parturition drape of claim 19, wherein the front panel and the interior panel are coextensive panels.

\* \* \* \* \*